US008288591B2

(12) United States Patent
Dershem

(10) Patent No.: US 8,288,591 B2
(45) Date of Patent: Oct. 16, 2012

(54) CURING AGENTS FOR EPOXY RESINS

(75) Inventor: Stephen M Dershem, San Diego, CA (US)

(73) Assignee: Designer Molecules, Inc., San Diego, CA (US)

(*) Notice: Subject to any disclaimer, the term of this patent is extended or adjusted under 35 U.S.C. 154(b) by 267 days.

(21) Appl. No.: 12/622,658

(22) Filed: Nov. 20, 2009

(65) Prior Publication Data
US 2010/0144977 A1 Jun. 10, 2010

Related U.S. Application Data

(60) Provisional application No. 61/116,299, filed on Nov. 20, 2008.

(51) Int. Cl.
C07C 211/00 (2006.01)
C08G 59/14 (2006.01)
C08L 63/00 (2006.01)
(52) U.S. Cl. .......... 564/315; 525/523; 528/98; 564/323
(58) Field of Classification Search .............. 528/98
See application file for complete search history.

(56) References Cited

U.S. PATENT DOCUMENTS

| 3,409,589 | A | 11/1968 | Kine |
| 3,901,845 | A | 8/1975 | Newbould |
| 4,395,462 | A | 7/1983 | Polmanteer |
| 4,705,716 | A | 11/1987 | Tang |
| 4,968,738 | A | 11/1990 | Dershem |
| 5,026,794 | A | 6/1991 | Ho et al. |
| 5,045,127 | A | 9/1991 | Dershem et al. |
| 5,064,480 | A | 11/1991 | Dershem et al. |
| 5,232,962 | A | 8/1993 | Dershem et al. |
| 5,250,629 | A | 10/1993 | Tani et al. |
| 5,306,333 | A | 4/1994 | Dershem et al. |
| 5,358,992 | A | 10/1994 | Dershem et al. |
| 5,403,389 | A | 4/1995 | Dershem |
| 5,418,290 | A | 5/1995 | Machida et al. |
| 5,447,988 | A | 9/1995 | Dershem et al. |
| 5,489,641 | A | 2/1996 | Dershem |
| 5,646,241 | A | 7/1997 | Dershem et al. |
| 5,714,086 | A | 2/1998 | Osuna et al. |
| 5,717,034 | A | 2/1998 | Dershem et al. |
| 5,718,941 | A | 2/1998 | Dershem et al. |
| 5,753,748 | A | 5/1998 | Dershem et al. |
| 5,861,111 | A | 1/1999 | Dershem et al. |
| 5,969,036 | A | 10/1999 | Dershem |
| 5,973,166 | A | 10/1999 | Mizori et al. |
| 5,990,210 | A | 11/1999 | Wideman et al. |
| 6,034,194 | A | 3/2000 | Dershem |
| 6,034,195 | A | 3/2000 | Dershem |
| 6,121,358 | A | 9/2000 | Dershem et al. |
| 6,172,142 | B1 * | 1/2001 | Lorenz et al. .............. 523/455 |
| 6,187,886 | B1 | 2/2001 | Husson et al. |
| 6,211,320 | B1 | 4/2001 | Dershem et al. |
| 6,369,183 | B1 | 4/2002 | Cook et al. |
| 6,383,653 | B1 | 5/2002 | Vaidya |
| 6,423,780 | B1 | 7/2002 | Dershem et al. |
| 6,429,281 | B1 | 8/2002 | Dershem et al. |
| 6,482,899 | B2 | 11/2002 | Ohashi et al. |
| 6,521,731 | B2 | 2/2003 | Dershem et al. |
| 6,620,946 | B2 | 9/2003 | Dershem et al. |
| 6,743,852 | B2 | 6/2004 | Dershem et al. |
| 6,750,301 | B1 | 6/2004 | Bonneau et al. |
| 6,790,597 | B2 | 9/2004 | Dershem |
| 6,825,245 | B2 | 11/2004 | Dershem |

(Continued)

FOREIGN PATENT DOCUMENTS

EP 1834969 9/2007

(Continued)

OTHER PUBLICATIONS

Computer generated English translation of JP 2005-111861 A, Yuzuriha et al, Apr. 28, 2005.*
Naeimi et al., 2006, "Mild and convenient one pot synthesis of Schiff bases in the presence of P2O5/Al2O3 as new catalyst under solvent-free conditions", Journal of Molecular Catalyst A: Chemical, vol. 260, p. 100-104.*
Adamson "Review of CSP and Flip Chip Underfill Processes and When to Use the Right Dispensing Tools for Efficient Manufacturing", Paper Presented at GlobalTRONICS Technology Conference,Singapore 2002, 1-6.
Mimura et al., "Characteristics of epoxy resin cured with in situ polymerized curing agen", Polymer 43: 2002, 7559-7566.

(Continued)

Primary Examiner — Peter F Godenschwager
Assistant Examiner — David Karst
(74) Attorney, Agent, or Firm — The Law Office of Jane K. Babin, Professional Corporation; Jane K. Babin

(57) ABSTRACT

A variety of curing agents for epoxy resins and methods for preparation thereof are disclosed, including compounds having the structures of formulas III and IV:

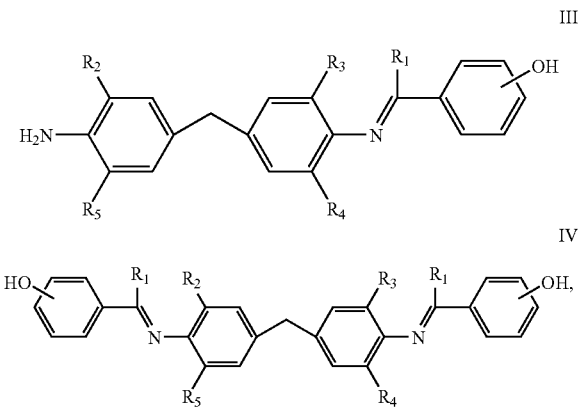

wherein each of $R_1$, $R_2$, $R_3$, $R_4$, and $R_5$ is independently selected from the group consisting of H, methyl, ethyl, n-propyl, iso-propyl, a butyl, and phenyl. Epoxy-based compositions including various curing agents are also disclosed. Other epoxy curatives containing amino, phenol, and/or imine groups are disclosed.

11 Claims, No Drawings

U.S. PATENT DOCUMENTS

| | | | |
|---|---|---|---|
| 6,831,132 B2 | 12/2004 | Liu et al. | |
| 6,852,814 B2 | 2/2005 | Dershem et al. | |
| 6,916,856 B2 | 7/2005 | Dershem | |
| 6,946,523 B2 | 9/2005 | Dershem et al. | |
| 6,960,636 B2 | 11/2005 | Dershem et al. | |
| 6,963,001 B2 | 11/2005 | Dershem et al. | |
| 7,102,015 B2 | 9/2006 | Dershem et al. | |
| 7,119,160 B2 | 10/2006 | Kodama et al. | |
| 7,157,587 B2 | 1/2007 | Mizori et al. | |
| 7,176,044 B2 | 2/2007 | Forray et al. | |
| 7,199,249 B2 | 4/2007 | Liu et al. | |
| 7,208,566 B2 | 4/2007 | Mizori et al. | |
| 7,285,613 B2 | 10/2007 | Dershem et al. | |
| 7,309,724 B2 | 12/2007 | Dershem et al. | |
| 7,517,925 B2 | 4/2009 | Dershem et al. | |
| 7,582,078 B2 | 9/2009 | Chen et al. | |
| 7,678,879 B2 | 3/2010 | Dershem | |
| 2002/0062923 A1 | 5/2002 | Forray | |
| 2002/0099168 A1 | 7/2002 | Dershem et al. | |
| 2002/0188137 A1 | 12/2002 | Dershem et al. | |
| 2002/0193541 A1 | 12/2002 | Dershem et al. | |
| 2002/0198356 A1 | 12/2002 | Dershem et al. | |
| 2003/0008992 A1 | 1/2003 | Dershem et al. | |
| 2003/0055121 A1 | 3/2003 | Dershem et al. | |
| 2003/0060531 A1 | 3/2003 | Dershem et al. | |
| 2003/0087999 A1 | 5/2003 | Dershem et al. | |
| 2003/0109666 A1 | 6/2003 | Dershem et al. | |
| 2003/0120077 A1 | 6/2003 | Galbo et al. | |
| 2003/0125551 A1 | 7/2003 | Dershem et al. | |
| 2003/0178138 A1 | 9/2003 | Taukagoshi | |
| 2003/0199638 A1 | 10/2003 | Liu et al. | |
| 2003/0208016 A1 | 11/2003 | Dershem et al. | |
| 2004/0006166 A1 | 1/2004 | Liu et al. | |
| 2004/0019224 A1 | 1/2004 | Dershem et al. | |
| 2004/0077798 A1 | 4/2004 | Dershem et al. | |
| 2004/0082724 A1 | 4/2004 | Dershem et al. | |
| 2004/0102566 A1 | 5/2004 | Forray et al. | |
| 2004/0123948 A1 | 7/2004 | Dershem et al. | |
| 2004/0225026 A1 | 11/2004 | Mizori et al. | |
| 2004/0225045 A1 | 11/2004 | Forray | |
| 2004/0225059 A1 | 11/2004 | Mizori et al. | |
| 2005/0107542 A1 | 5/2005 | Liu et al. | |
| 2005/0119362 A1 | 6/2005 | Ishikawa | |
| 2005/0136620 A1 | 6/2005 | Dershem et al. | |
| 2005/0137277 A1 | 6/2005 | Dershem et al. | |
| 2005/0267254 A1 | 12/2005 | Mizori et al. | |
| 2005/0272888 A1 | 12/2005 | Dershem et al. | |
| 2006/0009578 A1 | 1/2006 | Dershem | |
| 2006/0063014 A1 | 3/2006 | Forray | |
| 2006/0069232 A1 | 3/2006 | Dershem | |
| 2006/0089447 A1 | 4/2006 | Robertson et al. | |
| 2006/0142517 A1 | 6/2006 | Dershem | |
| 2006/0171981 A1 | 8/2006 | Richard et al. | |
| 2007/0042173 A1 | 2/2007 | Nagaoka et al. | |
| 2007/0117925 A1 | 5/2007 | Strickler et al. | |
| 2007/0155869 A1 | 7/2007 | Dershem et al. | |
| 2007/0205399 A1 | 9/2007 | Mizori | |
| 2007/0259782 A1 * | 11/2007 | Yamamoto et al. | 503/201 |
| 2007/0299154 A1 | 12/2007 | Dershem et al. | |
| 2008/0017308 A1 | 1/2008 | Dershem et al. | |
| 2008/0075961 A1 | 3/2008 | Mizori | |
| 2008/0075963 A1 | 3/2008 | Dershem | |
| 2008/0075965 A1 | 3/2008 | Dershem | |
| 2008/0103240 A1 | 5/2008 | Dershem | |
| 2008/0142158 A1 | 6/2008 | Dershem | |
| 2008/0146738 A1 | 6/2008 | Dershem | |
| 2008/0160315 A1 | 7/2008 | Forray et al. | |
| 2008/0191173 A1 | 8/2008 | Dershem et al. | |
| 2008/0210375 A1 | 9/2008 | Dershem et al. | |
| 2008/0251935 A1 | 10/2008 | Dershem | |
| 2008/0257493 A1 | 10/2008 | Dershem | |
| 2008/0262191 A1 | 10/2008 | Mizori | |
| 2009/0061244 A1 | 3/2009 | Dershem | |
| 2009/0215940 A1 | 8/2009 | Dershem | |
| 2009/0288768 A1 | 11/2009 | Dershem | |
| 2010/0041803 A1 | 2/2010 | Dershem | |
| 2010/0041823 A1 | 2/2010 | Dershem | |
| 2010/0041832 A1 | 2/2010 | Dershem | |
| 2010/0041845 A1 | 2/2010 | Dershem et al. | |
| 2010/0056671 A1 | 3/2010 | Dershem | |
| 2010/0063184 A1 | 3/2010 | Dershem | |

FOREIGN PATENT DOCUMENTS

| | | |
|---|---|---|
| JP | 02199127 | 8/1990 |
| JP | 04093318 | 3/1992 |
| JP | 2005111861 A * | 4/2005 |
| WO | 2004098625 | 11/2004 |
| WO | WO2004099331 | 11/2004 |
| WO | WO-2005121190 | 12/2005 |
| WO | WO-2007100329 | 9/2007 |
| WO | WO-2008077141 | 6/2008 |
| WO | WO-2008124797 | 10/2008 |
| WO | WO-2008130894 | 10/2008 |
| WO | 2008151437 | 12/2008 |
| WO | 2010018198 | 2/2010 |
| WO | WO-2010019832 | 2/2010 |
| WO | 2011116050 A2 | 9/2011 |

OTHER PUBLICATIONS

Nakamura et al., "Epoxy Resins (Curing Reactions)", Polymeric Materials Encyclopedia (Salamone ed; CRC Press, Boca Raton, FL) 1996, 2238-46.

Nakamura et al., "Thermal analysis of expoxy curing using polyfunctional active esters as curing agents", Thermochimica Acta 183: 1991, 269-277.

PCT International Search Report for PCT/US2011/028606 dated Feb. 21, 2012.

* cited by examiner

CURING AGENTS FOR EPOXY RESINS

CROSS REFERENCE TO RELATED APPLICATIONS

This application claims the benefit of priority under 35 USC §119 of U.S. Provisional Application Ser. No. 61/116,299 filed Nov. 20, 2008, the entire disclosure of which is incorporated herein by reference.

FIELD OF THE INVENTION

The present invention relates to curatives for epoxy resins, and compositions (e.g. adhesives) containing such resins cured using the same, methods of preparation and uses therefor. More specifically, the present invention relates to hybrid curatives for epoxy resins comprising both aromatic amine, phenol and/or phenyl ester moieties.

BACKGROUND OF THE INVENTION

As the electronics industry advances, and production of light weight components increases, the development of new materials gives producers increased options for further improving the performance and ease of manufacture of such components. Adhesive compositions are used for a variety of purposes in the fabrication and assembly of semiconductor packages and microelectronic devices. The more prominent uses include bonding of electronic elements such as integrated circuit (IC) chips to lead frames or other substrates, and bonding IC chips to other IC chips. Adhesives useful for electronic packaging applications typically exhibit properties such as good mechanical strength, curing properties that do not affect the component or the carrier, and rheological properties compatible with application to microelectronic and semiconductor components.

The demand for smaller and more powerful electronic components presents certain challenges to the microelectronic packaging industry. One way to include more semiconductor die in a component without increasing circuit board area is to arrange the die in a stacked configuration. Indeed, "stacked die" packages conserve "circuit board real estate" without sacrificing power or performance of the electronic component. In addition, the die used in stacked die applications are becoming ever thinner, requiring new adhesive solutions in order to preserve the integrity of these very thin die.

Moreover, other configurations of computer chips on circuit board such as those that require direct attachment to a substrate or board (e.g. "Flip Chips"), required similar properties to achieve higher speed and chip density on circuit boards. Yet with high density and direct contact between circuit boards and chips, there is concern about the thermomechanical expansion mismatch between the chip and the substrate or board, as well as concern that moisture can cause problems with tiny solder joints.

Glycidyl ether and glycidyl ester epoxy compounds have been commercially important as components of thermoset resins and adhesives for several decades. Not only can these reactive oxirane compounds be catalytically cured to yield cross-linked thermosets by themselves, but they can also be co-cured with a variety of other compounds (which are commonly referred to as epoxy curatives).

Primary amines and phenols are among the useful curative compounds for epoxy resins. Each primary amine can react twice with an epoxy functional group, while a phenol will react once. Di-functional primary amines, therefore are useful as cross-linking curatives for epoxies, while di-functional phenols tend to produce thermoplastic segments through chain extension. Aliphatic amines are potent curatives for epoxy compounds, but are usually far too reactive to be used in one-component adhesive compositions. Compounds that contain both aromatic amine and phenol functionality are know and available in commerce. These include the relatively low cost 2-aminophenol, 3-aminophenol, and 4-aminophenol isomeric compounds. Other compounds in this commercially available category of hybrid amine-phenol epoxy curatives includes 5-amino-1-naphthol. All of these compounds have been found to be too reactive as epoxy curatives and yield one-component blends with epoxy monomers that have been found to have insufficient pot life for practical one-component applications.

The microelectronics industry continues to require new adhesives that are able to meet its varying demands. Among those demand is a need to have better curatives for epoxy resins. Accordingly, there is a need for the development of materials to address the requirements of this rapidly evolving industry. Some of the commercially available lower molecular weight hybrid amine-phenol compounds are also relatively volatile and pose a health risk to the end user via inhalation of toxic vapors during curing operations. There remains a need, therefore, for hybrid curative compounds that have better pot life, and lower volatility.

SUMMARY OF THE INVENTION

This invention is directed to curing agents for epoxy resins. In some embodiments, there are provided compounds having the structures of formulas III and IV:

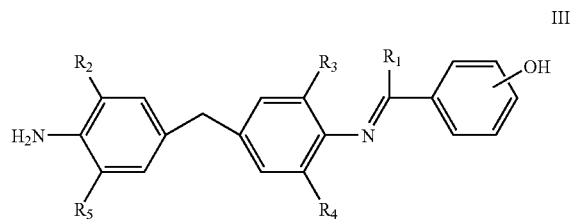

wherein each of $R_1$, $R_2$, $R_3$, $R_4$, and $R_5$ is independently selected from the group consisting of H, methyl, ethyl, n-propyl, iso-propyl, a butyl, and phenyl.

In other embodiments, there are provided compounds having the structure of formula V:

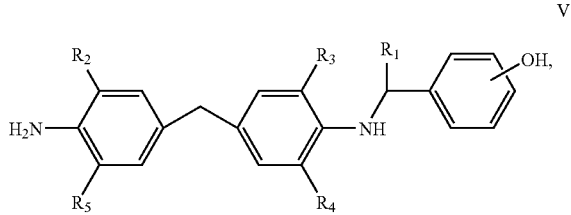

wherein each of $R_1$, $R_2$, $R_3$, $R_4$, $R_5$ is independently selected from the group consisting of H, methyl, ethyl, n-propyl, isopropyl, any butyl, or phenyl. Methods of making and using such compounds, such as for curing epoxy resins, are also provided. Particular species covered by generic stricture V are also disclosed.

In yet other embodiments, there are provided compounds having the structure XV:

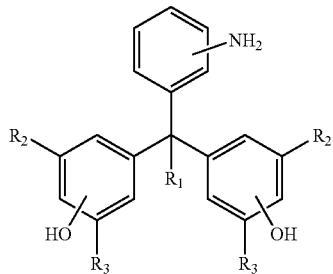

XV wherein $R_1$ is selected from the group consisting of H and a lower alkyl, and each of $R_2$ and $R_3$ is independently selected from the group consisting of Cl, Br, F, and a lower alkyl.

In further embodiments, there are provided compounds having the structure XVI:

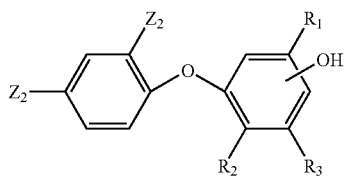

XVI wherein $Z_2$ is selected from the group consisting of H and $NH_2$, and each of $R_1$, $R_2$, and $R_3$ is independently selected from the group consisting of H and a lower alkyl.

In still other embodiments, there are provided methods of making and using such compounds, e.g., for curing epoxy resins, are also provided.

In additional embodiments, there are provided particular species covered by generic strictures III-V, XV and XVI are also disclosed, as well as other amino-phenol and/or amino-imine-phenol compounds useful for the same purposes.

DETAILED DESCRIPTION

It is to be understood that both the foregoing general description and the following detailed description are exemplary and explanatory only and are not restrictive of the invention claimed. As used herein, the use of the singular includes the plural unless specifically stated otherwise. As used herein, "or" means "and/or" unless stated otherwise. Furthermore, use of the term "including" as well as other forms, such as "includes," and "included," is not limiting. The section headings used herein are for organizational purposes only and are not to be construed as limiting the subject matter described.

Unless specific definitions are provided, the nomenclatures utilized in connection with, and the laboratory procedures and techniques of analytical chemistry, synthetic organic and inorganic chemistry described herein are those known in the art, such as those set forth in "IUPAC Compendium of Chemical Terminology: IUPAC Recommendations (The Gold Book)" (McNaught ed.; International Union of Pure and Applied Chemistry, $2^{nd}$ Ed., 1997) and "Compendium of Polymer Terminology and Nomenclature: IUPAC Recommendations 2008" (Jones et al., eds; International Union of Pure and Applied Chemistry, 2009). Standard chemical symbols are used interchangeably with the full names represented by such symbols. Thus, for example, the terms "hydrogen" and "H" are understood to have identical meaning Standard techniques may be used for chemical syntheses, chemical analyses, and formulation.

Terms, Definitions, and Abbreviations

The term "about" as used herein means that a number referred to as "about" comprises the recited number plus or minus 1-10% of that recited number. For example, "about" 100 degrees can mean 95-105 degrees or as few as 99-101 degrees depending on the situation. Whenever it appears herein, a numerical range such as "1 to 20" refers to each integer in the given range; e.g., "1 to 20 carbon atoms" means that an alkyl group can contain only 1 carbon atom, 2 carbon atoms, 3 carbon atoms, etc., up to and including 20 carbon atoms (although the term "alkyl" also includes instances where no numerical range of carbon atoms is designated).

The terms "adhesive" or "adhesive compound" as used herein, refers to any substance that can adhere or bond two items together. Implicit in the definition of an "adhesive composition" or "adhesive formulation" is the fact that the composition or formulation is a combination or mixture of more than one species, component or compound, which can include adhesive monomers, oligomers, and/or polymers along with other materials, whereas an "adhesive compound" refers to a single species, such as an adhesive polymer or oligomer. More specifically, adhesive composition refers to un-cured mixtures in which the individual components in the mixture retain the chemical and physical characteristics of the original individual components of which the mixture is made. Adhesive compositions are typically malleable and may be liquids, paste, gel or another form that can be applied to an item so that it can be bonded to another item.

"Cured adhesive," "cured adhesive composition" or "cured adhesive compound" refers to adhesives components and mixtures obtained from reactive curable original compound(s) or mixture(s) thereof which have undergone a chemical and/or physical changes such that the original compound(s) or mixture(s) is(are) transformed into a solid, substantially non-flowing material. A typical curing process may involve crosslinking.

The term "curable" means that an original compound(s) or composition material(s) can be transformed into a solid, substantially non-flowing material by means of chemical reaction, crosslinking, radiation crosslinking, or the like. Thus, adhesive compositions of the invention are curable, but unless otherwise specified, the original compound(s) or composition material(s) is(are) not cured.

The term "photoimageable", as used herein, refers to the ability of a compound or composition to be selectively cured only in areas exposed to light. The exposed areas of the compound are thereby rendered cured and insoluble, while the unexposed area of the compound or composition remain un-cured and therefore soluble in a developer solvent. Typically, this operation is conducted using ultraviolet light as the light source and a photomask as the means to define where the exposure occurs. The selective patterning of dielectric layers on a silicon wafer can be carried out in accordance with various photolithographic techniques known in the art. In one method, a photosensitive polymer film is applied over the desired substrate surface and dried. A photomask containing the desired patterning information is then placed in close proximity to the photoresist film. The photoresist is irradiated through the overlying photomask by one of several types of imaging radiation including UV light, e-beam electrons, x-rays, or ion beam. Upon exposure to the radiation, the polymer film undergoes a chemical change (crosslinks) with concomitant changes in solubility. After irradiation, the substrate is soaked in a developer solution that selectively removes the non-crosslinked or unexposed areas of the film.

The term "passivation" as used herein, refers to the process of making a material "passive" in relation to another material or condition. The term "passivation layers" refers to layers that are commonly used to encapsulate semiconductor devices, such as semiconductor wafers, to isolate the device from its immediate environment and, thereby, to protect the device from oxygen, water, etc., as well airborne or space-borne contaminants, particulates, humidity and the like. Passivation layers are typically formed from inert materials that are used to coat the device. This encapsulation process also passivates semiconductor devices by terminating dangling bonds created during manufacturing processes and by adjusting the surface potential to either reduce or increase the surface leakage current associated with these devices. In certain embodiments of the invention, passivation layers (PLs) contain dielectric material that is disposed over a microelectronic device. Such PLs are typically patterned to form openings therein that provide for making electrical contact to the microelectronic device. Often a passivation layer is the last dielectric material disposed over a device and serves as a protective layer.

The term "Interlayer Dielectric Layer" (ILD) refers to a layer of dielectric material disposed over a first pattern of conductive traces and between such first pattern and a second pattern of conductive traces. Such ILD layer is typically patterned to form openings therein (generally referred to as "vias") to provide for electrical contact between the first and second patterns of conductive traces in specific regions. Other regions of such ILD layer are devoid of vias and thus prevent electrical contact between the conductive traces of the first and second patterns in such other regions.

The term "thermoplastic," as used herein, refers to the ability of a compound, composition or other material (e.g. a plastic) to dissolve in a suitable solvent or to melt to a liquid when heated and freeze to a solid, often brittle and glassy, state when cooled sufficiently.

The term "thermoset," as used herein, refers to the ability of a compound, composition or other material to irreversibly "cure" resulting in a single tridimensional network that has greater strength and less solubility compared to the non-cured product. Thermoset materials are typically polymers that may be cured, for example, through heat (e.g. above 200° C.), via a chemical reaction (e.g. epoxy ring-opening, free-radical polymerization, etc or through irradiation (e.g. visible light, UV light, electron beam radiation, ion-beam radiation, or X-ray irradiation). Thermoset materials, such as thermoset polymers or resins, are typically liquid or malleable forms prior to curing, and therefore may be molded or shaped into their final form, and/or used as adhesives. Curing transforms the thermoset resin into a rigid infusible and insoluble solid or rubber by a cross-linking process. Thus, energy and/or catalysts are typically added that cause the molecular chains to react at chemically active sites (unsaturated or epoxy sites, for example), linking the polymer chains into a rigid, 3-D structure. The cross-linking process forms molecules with a higher molecular weight and resultant higher melting point. During the reaction, when the molecular weight of the polymer has increased to a point such that the melting point is higher than the surrounding ambient temperature, the polymer becomes a solid material.

The term "cross-linking," as used herein, refers to the attachment of two or more oligomer or longer polymer chains by bridges of an element, a molecular group, a compound, or another oligomer or polymer. Cross-linking may take place upon heating or exposure to light; some cross-linking processes may also occur at room temperature or a lower temperature. As cross-linking density is increased, the properties of a material can be changed from thermoplastic to thermosetting.

As used herein, "B-stageable" refers to the properties of an adhesive having a first solid phase followed by a tacky rubbery stage at elevated temperature, followed by yet another solid phase at an even higher temperature. The transition from the tacky rubbery stage to the second solid phase is thermosetting. However, prior to thermosetting, the material behaves similarly to a thermoplastic material. Thus, such adhesives allow for low lamination temperatures while providing high thermal stability.

A "die" or "semiconductor die" as used herein, refers to a small block of semiconducting material, on which a functional circuit is fabricated.

A "flip-chip" semiconductor device is one in which a semiconductor die is directly mounted to a wiring substrate, such as a ceramic or an organic printed circuit board. Conductive terminals on the semiconductor die, usually in the form of solder bumps, are directly physically and electrically connected to the wiring pattern on the substrate without use of wire bonds, tape-automated bonding (TAB), or the like. Because the conductive solder bumps making connections to the substrate are on the active surface of the die or chip, the die is mounted in a face-down manner, thus the name "flip-chip."

The terms "underfill," "underfill composition" and "underfill material" are used interchangeably to refer to a material, typically polymeric compositions, used to fill gaps between a semiconductor component, such as a semiconductor die, and a substrate. The term "underfilling" refers to the process of applying an underfill composition to a semiconductor component-substrate interface, thereby filling the gaps between the component and the substrate.

The term "monomer" refers to a molecule that can undergo polymerization or copolymerization thereby contributing constitutional units to the essential structure of a macromolecule (a polymer).

"Polymer" and "polymer compound" are used interchangeably herein, to refer generally to the combined the products of a single chemical polymerization reaction. Polymers are produced by combining monomer subunits into a covalently bonded chain. Polymers that contain only a single type of monomer are known as "homopolymers," while polymers containing a mixture of monomers are known as "copolymers."

The term "copolymers" is inclusive of products that are obtained by copolymerization of two monomer species, those obtained from three monomers species (terpolymers), those obtained from four monomers species (quaterpolymers), etc. It is well known in the art that copolymers synthesized by chemical methods include, but are not limited to, molecules with the following types of monomer arrangements:

alternating copolymers, which contain regularly alternating monomer residues; periodic copolymers, which have monomer residue types arranged in a repeating sequence;

random copolymers, which have a random sequence of monomer residue types; statistical copolymers, which have monomer residues arranged according to a known statistical rule;

block copolymers, which have two or more homopolymer subunits linked by covalent bonds. The blocks of homopolymer within block copolymers, for example, can be of any length and can be blocks of uniform or variable length. Block copolymers with two or three distinct blocks are called diblock copolymers and triblock copolymers, respectively; and star copolymers, which have chains of monomer residues having different constitutional or configurational features that are linked through a central moiety.

The skilled artisan will appreciate that a single copolymer molecule may have different regions along its length that can be characterized as an alternating, periodic, random, etc. A copolymer product of a chemical polymerization reaction may contain individual polymeric fragments that each differ in the arrangement of monomer units. The skilled artisan will further be knowledgeable in methods for synthesizing each of these types of copolymers, and for varying reaction conditions to favor one type over another.

Furthermore, the length of a polymer chain according to the present invention, will typically vary over a range or average size produced by a particular reaction. The skilled artisan will be aware, for example, of methods for controlling the average length of a polymer chain produced in a given reaction and also of methods for size-selecting polymers after they have been synthesized.

Unless a more restrictive term is used, polymer is intended to encompass homopolymers, and copolymers having any arrangement of monomer subunits as well as copolymers containing individual molecules having more than one arrangement. With respect to length, unless otherwise indicated, any length limitations recited for the polymers described herein are to be considered averages of the lengths of the individual molecules in polymer.

The term "thermoplastic elastomer" or "TPE", as used herein refers to a class of copolymers that consist of materials with both thermoplastic and elastomeric properties.

The terms "hard blocks" or "hard segments" as used herein refer to a block of a copolymer (typically a thermoplastic elastomer) that is hard at room temperature by virtue of a of high melting point ($T_m$) or $T_g$. By contrast, the terms "soft blocks" or "soft segments" have a $T_g$ below room temperature.

As used herein, the terms "oligomer" or "oligomeric" refers to a polymer having a finite and moderate number of repeating monomers structural units. Oligomers of the invention typically have 2 to about 100 repeating monomer units; frequently 2 to about 30 repeating monomer units; and often 2 to about 10 repeating monomer units; and usually have a molecular weight up to about 3,000.

The skilled artisan will appreciate that oligomers and polymers may, depending on the availability of polymerizable groups or side chains, subsequently be incorporated as monomers in further polymerization or cross-linking reactions.

As used herein, the term "aliphatic" refers to any alkyl, alkenyl, cycloalkyl, or cycloalkenyl moiety.

The terms "aromatic hydrocarbon" or "aromatic" as used herein, refer to compounds having one or more benzene rings.

The term "alkane," as used herein, refers to saturated straight-chain, branched or cyclic hydrocarbons having only single bonds. Alkanes have general formula $CH_{2n+2}$.

As used herein, the term "alkyl" refers to straight or branched chain hydrocarbyl groups having from 1 up to about 500 carbon atoms. The term "lower alkyl" refers generally to alkyl groups having 1 to 6 carbon atoms. The terms "alkyl" and "substituted alkyl" include, respectively, substituted and unsubstituted $C_1$-$C_{500}$ straight chain saturated aliphatic hydrocarbon groups, substituted and unsubstituted $C_2$-$C_{200}$ straight chain unsaturated aliphatic hydrocarbon groups, substituted and unsubstituted $C_4$-$C_{100}$ branched saturated aliphatic hydrocarbon groups, substituted and unsubstituted $C_1$-$C_{500}$ branched unsaturated aliphatic hydrocarbon groups. For example, the definition of "alkyl" includes but is not limited to: methyl (Me), ethyl (Et), propyl (Pr), butyl (Bu), pentyl, hexyl, heptyl, octyl, nonyl, decyl, undecyl, ethenyl, propenyl, butenyl, penentyl, hexenyl, heptenyl, octenyl, nonenyl, decenyl, undecenyl, isopropyl (i-Pr), isobutyl (i-Bu), tert-butyl (t-Bu), sec-butyl (s-Bu), isopentyl, neopentyl, cyclopropyl, cyclobutyl, cyclopentyl, cyclohexyl, cycloheptyl, cyclooctyl, cyclopentenyl, cyclohexenyl, cycloheptenyl, cyclooctenyl, methylcyclopropyl, ethylcyclohexenyl, butenylcyclopentyl, tricyclodecyl, adamantyl, norbornyl and the like.

The term "substituted alkyl" refers to alkyl moieties bearing substituents that include but are not limited to alkyl, alkenyl, alkynyl, hydroxy, oxo, alkoxy, mercapto, cycloalkyl, substituted cycloalkyl, heterocyclic, substituted heterocyclic, aryl, substituted aryl (e.g., aryl$C_{1-10}$alkyl or aryl$C_{1-10}$alkyloxy), heteroaryl, substituted heteroaryl (e.g., heteroaryl$C_{1-10}$alkyl), aryloxy, substituted aryloxy, halogen, haloalkyl (e.g., trihalomethyl), cyano, nitro, nitrone, amino, amido, carbamoyl, =CH—, —C(O)H, —C(O)O—, —C(O)—, —S—, —S(O)$_2$, —OC(O)—O—, —NR—C(O)—, —NR—C(O)—NR—, —OC(O)—NR—, where R is H or lower alkyl, acyl, oxyacyl, carboxyl, carbamate, sulfonyl, sulfonamide, sulfuryl, $C_{1-10}$alkylthio, aryl$C_{1-10}$alkylthio, $C_{1-10}$alkylamino, aryl$C_{1-10}$alkylamino, N-aryl-N—$C_{1-10}$alkylamino, $C_{1-10}$alkyl carbonyl, aryl$C_{1-10}$alkylcarbonyl, $C_{1-10}$alkylcarboxy, aryl $C_{1-10}$alkylcarboxy, $C_{1-10}$alkyl carbonylamino, aryl $C_{1-10}$alkylcarbonylamino, tetrahydrofuryl, morpholinyl, piperazinyl, and hydroxypyronyl.

As used herein, the term "aryl" represents an unsubstituted, mono-, di- or trisubstituted monocyclic, polycyclic, biaryl aromatic groups covalently attached at any ring position capable of forming a stable covalent bond, certain preferred points of attachment being apparent to those skilled in the art (e.g., 3-phenyl, 4-naphtyl and the like). The aryl substituents are independently selected from the group consisting of halo, —OH, —SH, —CN, —NO$_2$, trihalomethyl, hydroxypyronyl, $C_{1-10}$alkyl, aryl$C_{1-10}$alkyl, $C_{1-10}$alkyloxy$C_{1-10}$alkyl, aryl$C_{1-10}$alkyloxy$C_{1-10}$alkyl, $C_{1-10}$alkylthio$C_{1-10}$alkyl, aryl$C_{1-10}$alkylthio$C_{1-10}$alkyl, $C_{1-10}$alkylamino$C_{1-10}$alkyl, aryl$C_{1-10}$alkylamino$C_{1-10}$alkyl, N-aryl-N—$C_{1-10}$alkylamino$C_{1-10}$alkyl, $C_{1-10}$alkylcarbonyl$C_{1-10}$alkyl, aryl $C_{1-10}$alkylcarbonyl $C_{1-10}$alkyl, $C_{1-10}$alkylcarboxy$C_{1-10}$alkyl, aryl$C_{1-10}$alkylcarboxy$C_{1-10}$alkyl, $C_{1-10}$alkylcarbonylamino$C_{1-10}$alkyl, and aryl$C_{1-10}$alkylcarbonylamino$C_{1-10}$alkyl.

Some specific examples of moieties encompassed by the definition of "aryl" include but are not limited to phenyl, biphenyl, naphthyl, dihydronaphthyl, tetrahydronaphthyl, indenyl, indanyl, azulenyl, anthryl, phenanthryl, fluorenyl, pyrenyl and the like. "Substituted aryl" refers to aryl groups further bearing one or more substituents as set forth below.

As used herein, the term "phenol" includes compounds having one or more phenolic functions per molecule. The terms aliphatic, cycloaliphatic and aromatic, when used to describe phenols, refers to phenols to which aliphatic, cycloaliphatic and aromatic residues or combinations of these backbones are attached by direct bonding or ring fusion.

As used herein, the terms "oxiranylene" or "epoxy" refer to divalent moieties having the structure:

The term "epoxy" also refers to thermosetting epoxide polymers that cure by polymerization and crosslinking when mixed with a catalyzing agent or "hardener," also referred to as a "curing agent" or "curative." Epoxies of the present invention include, but are not limited to aliphatic, cycloaliphatic, glycidyl ether, glycidyl ester, glycidyl amine epoxies, and the like.

The term "pot life" refers to the storage longevity of a composition and is measured as a change in viscosity as a function of storage time at room temperature.

As used herein, the term "free radical initiator" refers to any chemical species which, upon exposure to sufficient energy (e.g., light, heat, or the like), decomposes into parts which are uncharged, but every one of such part possesses at least one unpaired electron.

As used herein, the term "coupling agent" refers to chemical species that are capable of bonding to a mineral surface and which also contain polymerizably reactive functional group(s) so as to enable interaction with the adhesive composition. Coupling agents thus facilitate linkage of the die-attach paste to the substrate to which it is applied.

The term "diamine," as used herein, refers generally to a compound or mixture of compounds, where each species has 2 amine groups.

The term "diol" according to the present invention, is a compound containing two hydroxyl groups (—OH groups); while the term "polyol" refers to alcohols containing multiple hydroxyl groups.

The term "imine" refers a functional group containing a carbon-nitrogen double bond $R_1R_2C=N—R$, or to organic compounds that include such a functional group. Imines are also known as "Schiff bases" (or, alternatively, azomethines), and the nitrogen atom is connected to the group R, which is an aryl or alkyl group, but not hydrogen. Imines are typically synthesized by the nucleophilic addition of an amine to a ketone or aldehyde, resulting in two specific classes of imines, "ketimines" or "aldimines," respectively.

The term "solvent," as used herein, refers to a liquid that dissolves a solid, liquid, or gaseous solute, resulting in a solution. "Co-solvent" refers to a second, third, etc. solvent used with a primary solvent.

As used herein, the terms "polar protic solvents" refer to solvents that contain an O—H or N—H bond, while the terms "polar aprotic solvents" refer to solvents that do not contain an O—H or N—H bond.

As used herein, the term "alcohol catalyst" refers to an alcohol or combination of alcohols that, when added to a chemical reaction, has the effect of accelerating, increasing the rate or yield of the reaction without being consumed by the overall reaction. Typically, an alcohol catalyst will contain a single alcohol, but mixtures comprising two or more alcohols are contemplated for use in the present invention.

As used herein, "acid catalyst" refers to any acidic substance or compound that, when added to a chemical reaction, has the effect of accelerating, increasing the rate or yield of the reaction without being consumed by the overall reaction. Typically, an acid catalyst will contain a single acid, but mixtures comprising two or more acids are contemplated for use in the present invention. Acid catalysts of the invention can be soluble or insoluble. For example, polymer-bound acid catalysts may conveniently be used in the methods of the invention and then easily removed e.g. by gravity filtration.

The term "glass transition temperature" or "$T_g$" is used herein to refer to the temperature at which an amorphous solid, such as a polymer, becomes brittle on cooling, or soft on heating. More specifically, it defines a pseudo second order phase transition in which a supercooled melt yields, on cooling, a glassy structure and properties similar to those of crystalline materials e.g. of an isotropic solid material.

The terms "modulus" or "Young's modulus" as used herein, refer to a measure of the stiffness of a material. Within the limits of elasticity, modulus is the ratio of the linear stress to the linear strain which can be determined from the slope of a stress-strain curve created during tensile testing.

The term "Coefficient of Thermal Expansion" or abbreviation "CTE" are terms of art describing a thermodynamic property of a substance. The CTE relates a change in temperature to the change in a material's linear dimensions. As used herein "$\alpha_1$ CTE" or "$\alpha_1$" refers to the CTE before the $T_g$, while "$\alpha_2$ CTE" refers to the CTE after the $T_g$.

The term "thermogravimetric analysis" or abbreviation "TGA" refer to a method of testing and analyzing a material to determine changes in weight of a sample that is being heated in relation to change in temperature. The term "decomposition onset" refers to a temperature when the loss of weight in response to the increase of the temperature indicates that the sample is beginning to degrade.

According to embodiments of the present invention, a useful series of amine-phenol and/or imine-phenol hybrid curatives can be prepared in which both imino, phenolic and/or amino functionalities are combined within the same molecule. Furthermore, the ratio of total imino, phenolic and/or amino functionality can be adjusted over a wide range to yield either higher or lower cross-link densities. The reactivity of the imino functionality in these curatives can be controlled through the use of bulky substituents to control the reactivity of the amine and/or phenol.

One class of hybrid imine-phenol or amino-imine-phenol compounds of this invention is produced through the condensation of aromatic diamines with hydroxy-substituted aromatic aldehydes or ketones. The condensation products of these reactions are aldimines or ketimines, respectively. One method that may be used to form the imines is through direct condensation of a diamine with a carbonyl compound.

The reaction can be generally carried out thermally (i.e., no catalyst is required), for example, at temperatures between about 125° C. and about 180° C. in the presence of an azeotropic solvent, and under an inert gas blanket. The reaction is monitored by the rate of water generated and collected in the trap. The reaction is generally complete after 2 to 36 hours of reflux. Such a reaction is illustrated in the reaction Scheme A:

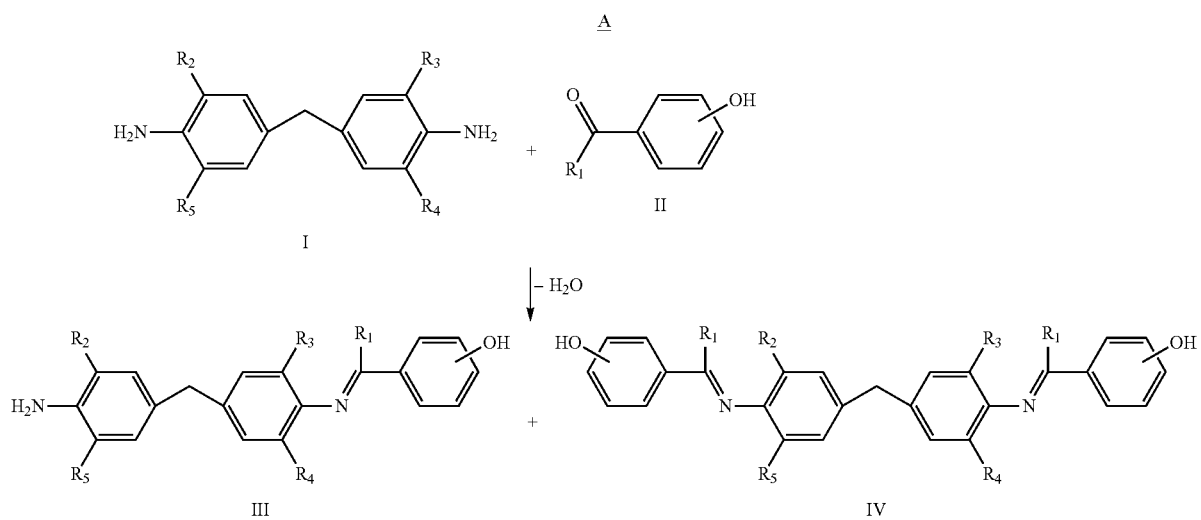

wherein each of $R_1$, $R_2$, $R_3$, $R_4$, $R_5$ is, independently, H, methyl, ethyl, n-propyl, iso-propyl, any butyl, or phenyl.

The reaction shown by the reaction scheme A may be carried out at various ratios of the starting compounds having general structures I and II. For example, a 1:1 mole ratio of the starting compounds of general structures I and II would result in a 1:2:1 statistical distribution of compounds of general structures I, III, and IV. In some embodiments, the ratio of the three components could be skewed toward higher levels of compound of general structure I depending on the initial mole ratio of compound of general structure I to compound of general structure II used in the reaction illustrated by the reaction scheme A. Reaction products skewed toward compound of general structure I are expected to have higher cross-link density, higher glass transition temperatures and higher modulus.

In other embodiments, the ratio of the three components could be skewed toward higher levels of compound of general structure IV, also depending on the initial mole ratio of compound of general structure I to compound of general structure II used in the reaction illustrated by the reaction scheme A. Reaction products skewed toward compound of general structure IV would have lower cross-link density, greater toughness and lower modulus. The general structure III includes both aromatic amine, imine, and phenol residues in the same molecule and therefore provides a hybrid curative which incorporates the desirable aspects of both of these types of curative functionalities.

Exemplary compounds that are contemplated in this invention and produced by the reaction scheme A include, but are not limited to, any of the following compounds (only structures that correspond to the statistically predominant form III are shown):

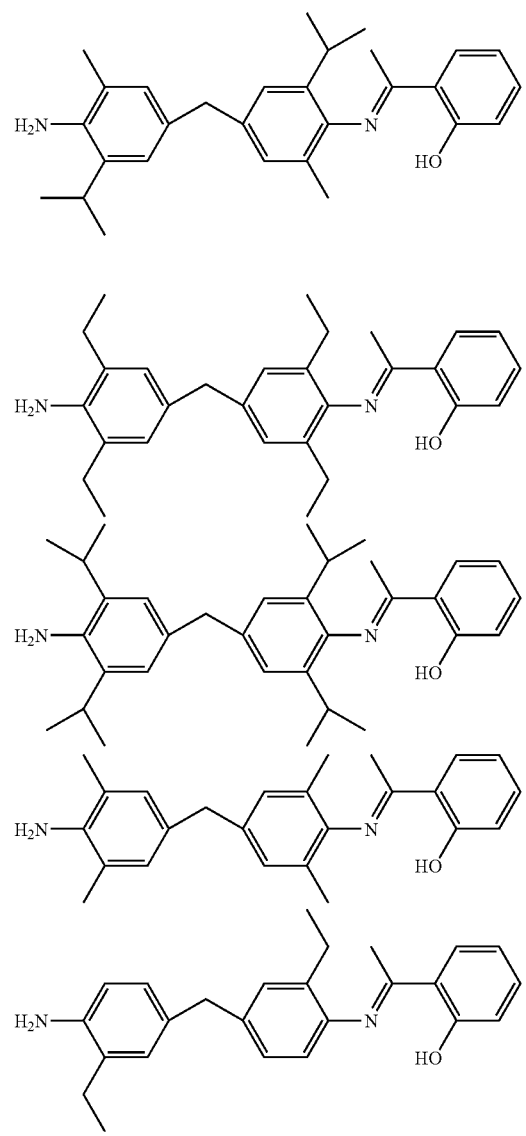

Other useful compounds that are contemplated in this invention and produced by the reaction scheme A include, but are not limited to, any of the following compounds (also, only structures that correspond to the statistically predominant form III are shown):
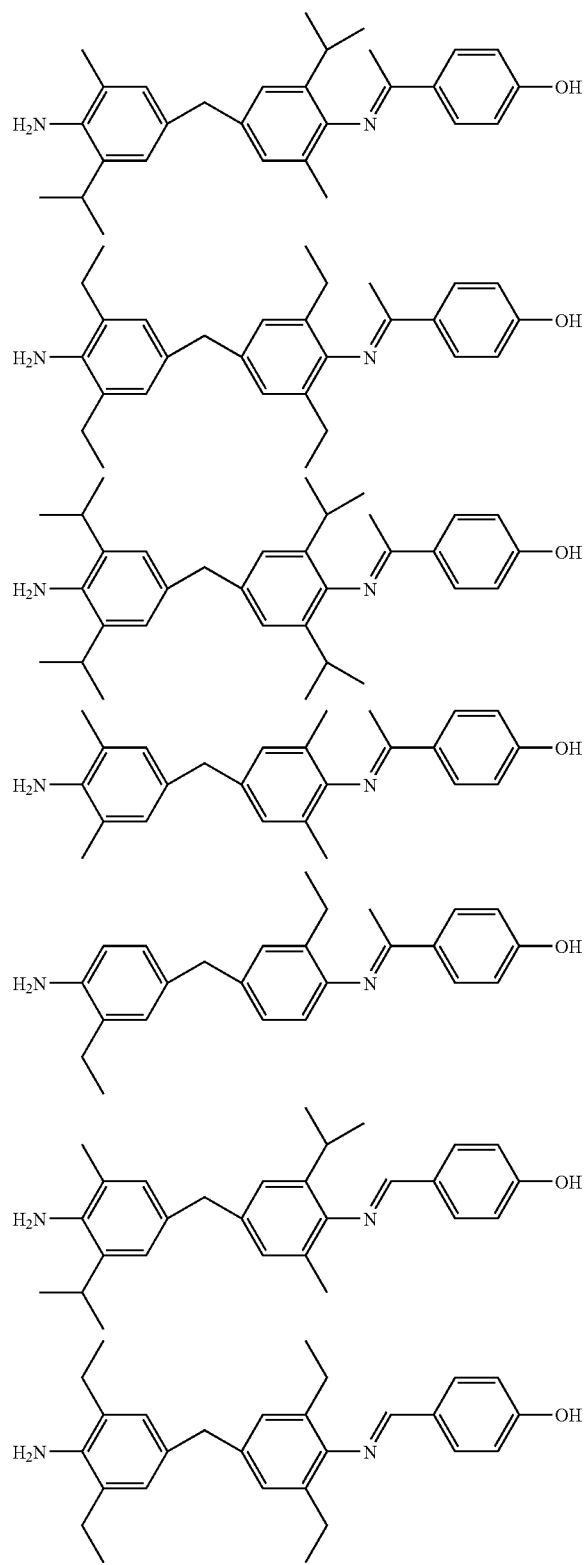
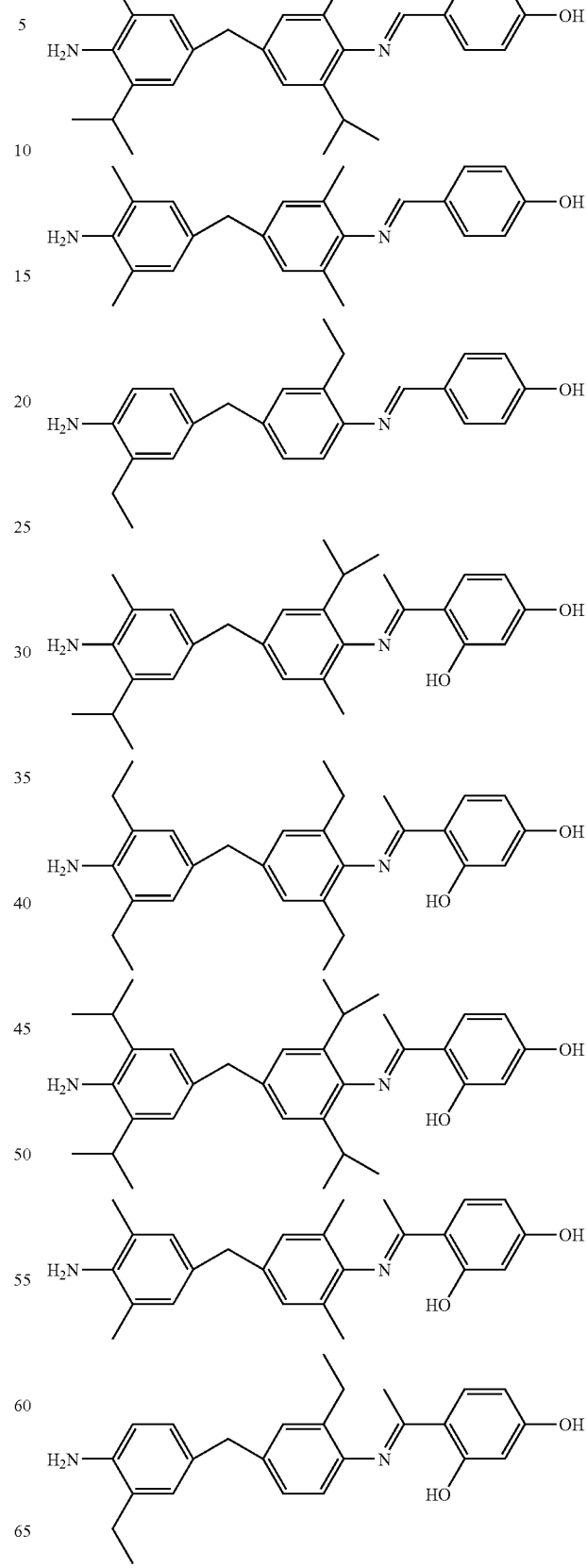

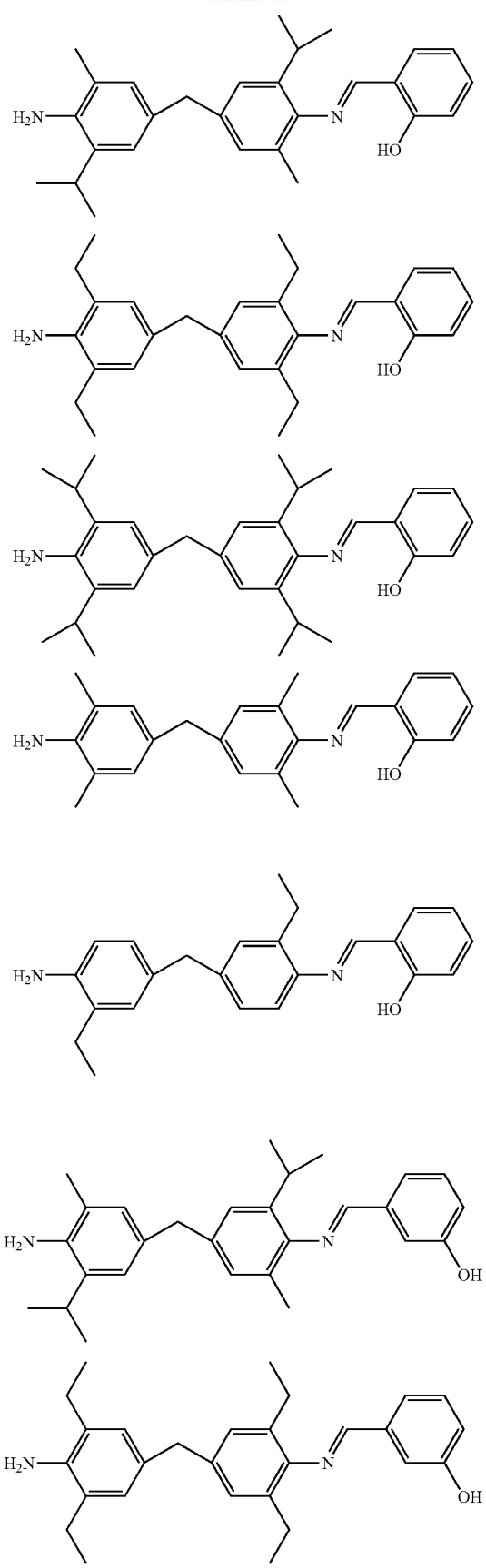
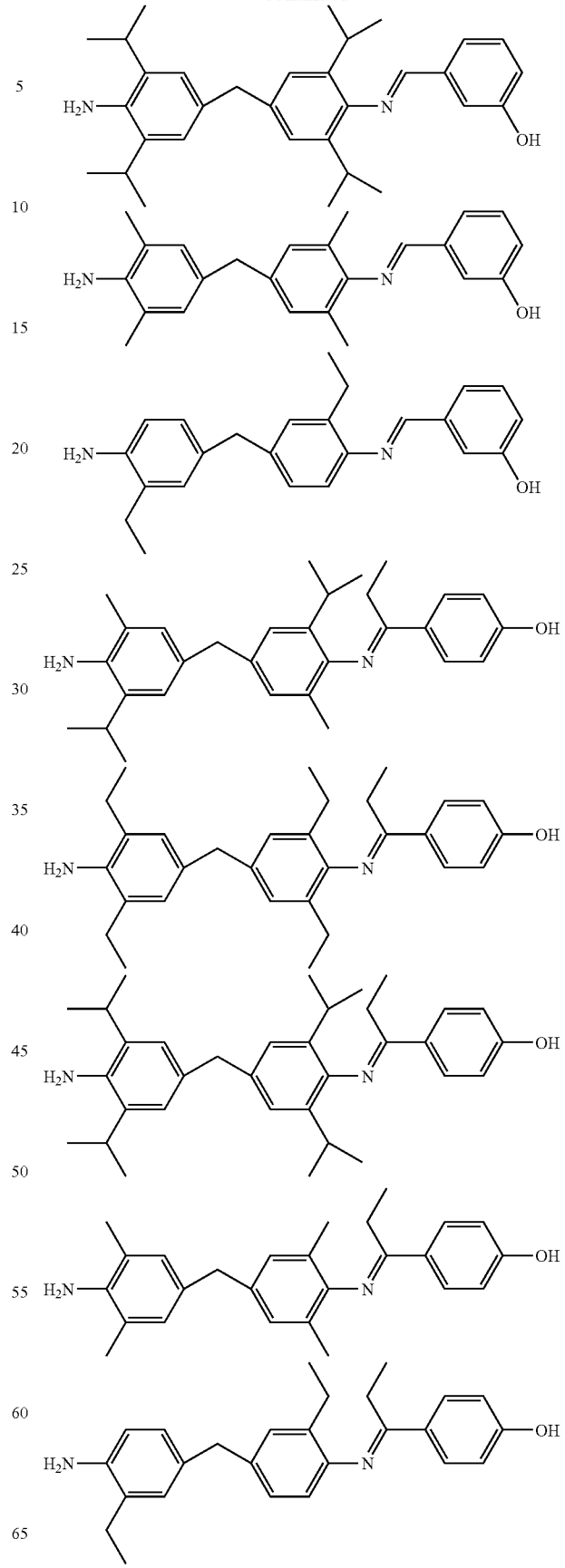

17
-continued
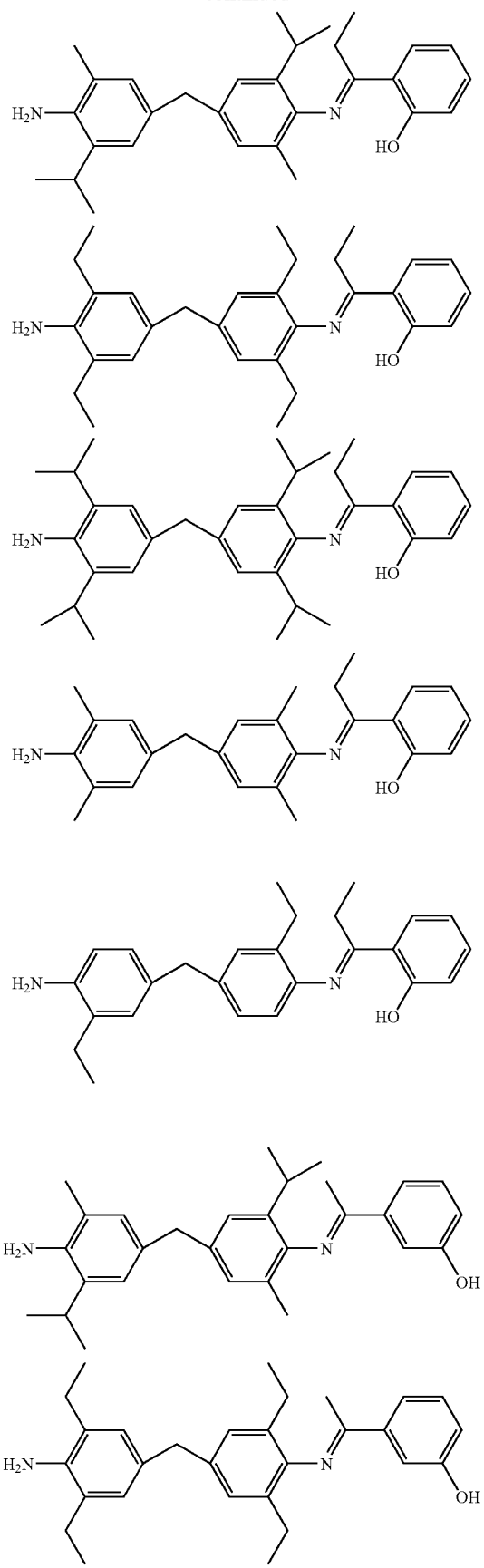
18
-continued
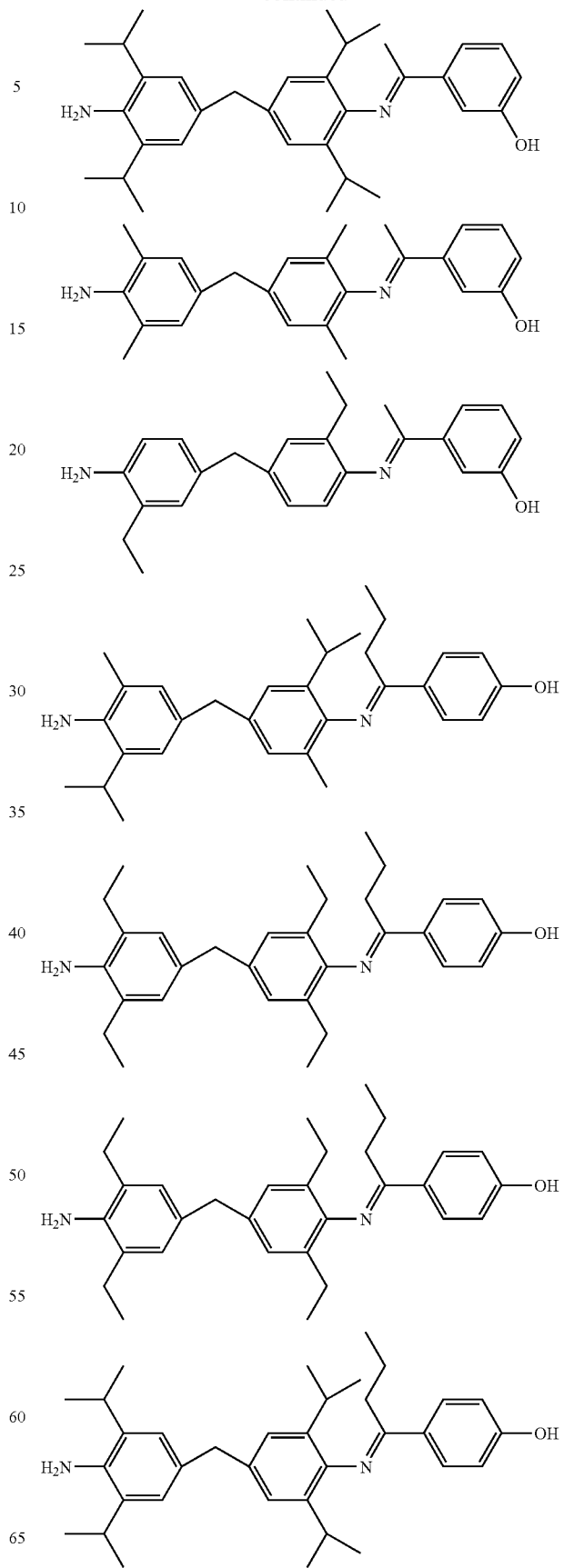

-continued

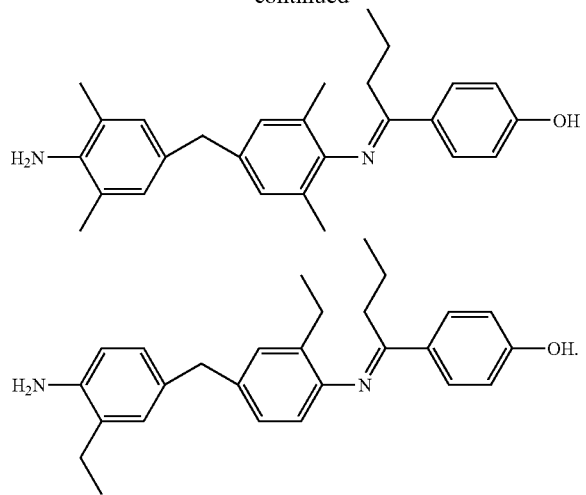

According to other embodiments of the present invention, the compounds having general structures III or IV shown on the reaction scheme A can be hydrogenated. As a result, the imine carbon-nitrogen double bond is reduced to produce another useful class of amine-phenol hybrid curatives. This reduction of the imine linkages, and the resulting compounds are illustrated by the reaction scheme B:

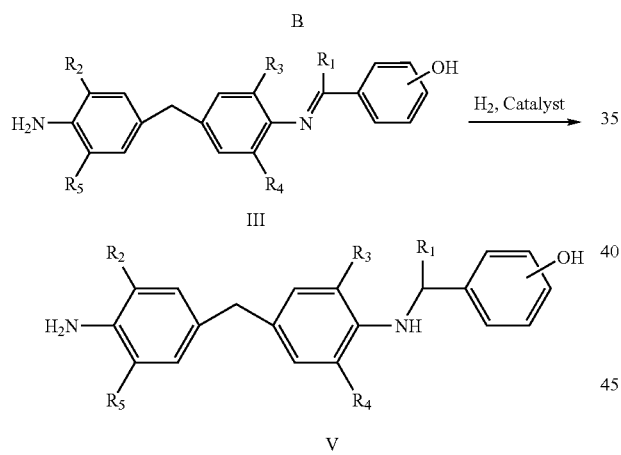

wherein each of $R_1$, $R_2$, $R_3$, $R_4$, $R_5$ is, independently, H, methyl, ethyl, n-propyl, iso-propyl, any butyl, or phenyl.

The reduction shown by the reaction scheme B could be accomplished using a variety of catalysts. Palladium on carbon may be used, but Pd, Pt, Ru or Rh (as free finely divided metals or on supports such as carbon, alumina, barium sulfate, calcium carbonate, or strontium carbonate) may also be used. Other hydrogenation catalysts that can be used include Raney nickel and copper chromite. Hydrogenation may be performed in an autoclave at a temperature between about 70° C. and about 140° C. at a pressure between about 30 and about 450 psi (i.e., between about 0.21 MPa and about 3.1 MPa). The reaction may be expected to be completed within six hours or less. The rate of the reaction could be monitored by the rate of consumption of hydrogen (via pressure drop).

As can be seen from the reaction scheme B, the starting compound is compound having general structure III, and the product of the reduction of the imine double bond generates compound having general structure V, comprising phenol, primary amine and secondary amine functionalities. Compound having general structure V thus has a new secondary amine epoxy curative site and, accordingly, reduces the hardener equivalent weight (HEW) of the molecule. The reduction of the carbon-nitrogen double bond also eliminates any possibility of hydrolysis of compound having general structure III (i.e. the reverse of the reaction scheme A).

Exemplary compounds that are contemplated in this invention, and produced by the reaction scheme B include, but are not limited to, any of the following compounds (only structures that correspond to the statistically predominant form are shown):

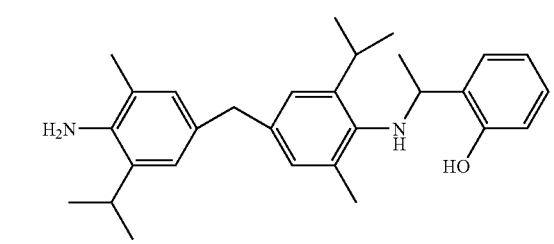

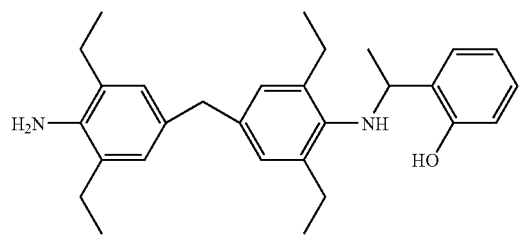

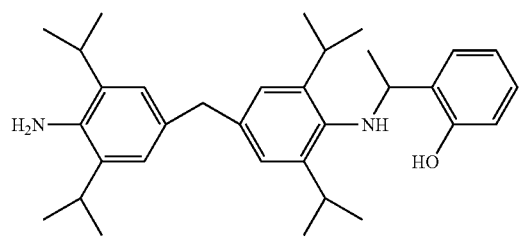

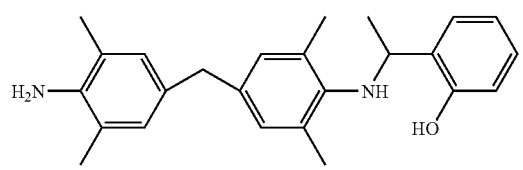

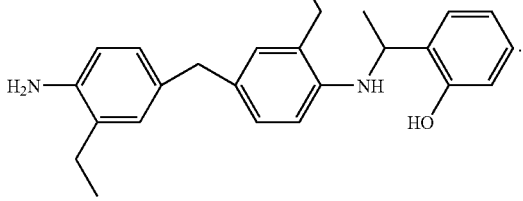

Other useful compounds that are contemplated in this invention and produced by the reaction scheme B include, but are not limited to, any of the following compounds (again, only structures that correspond to the statistically predominant form are shown):
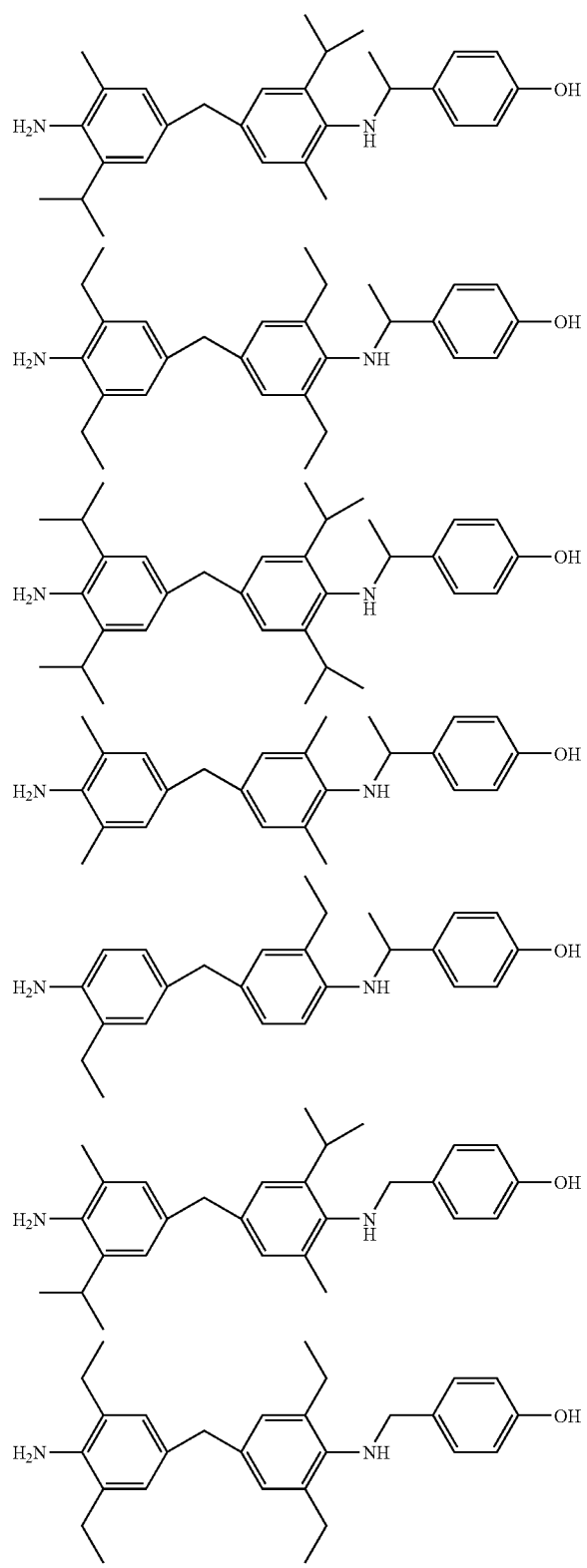
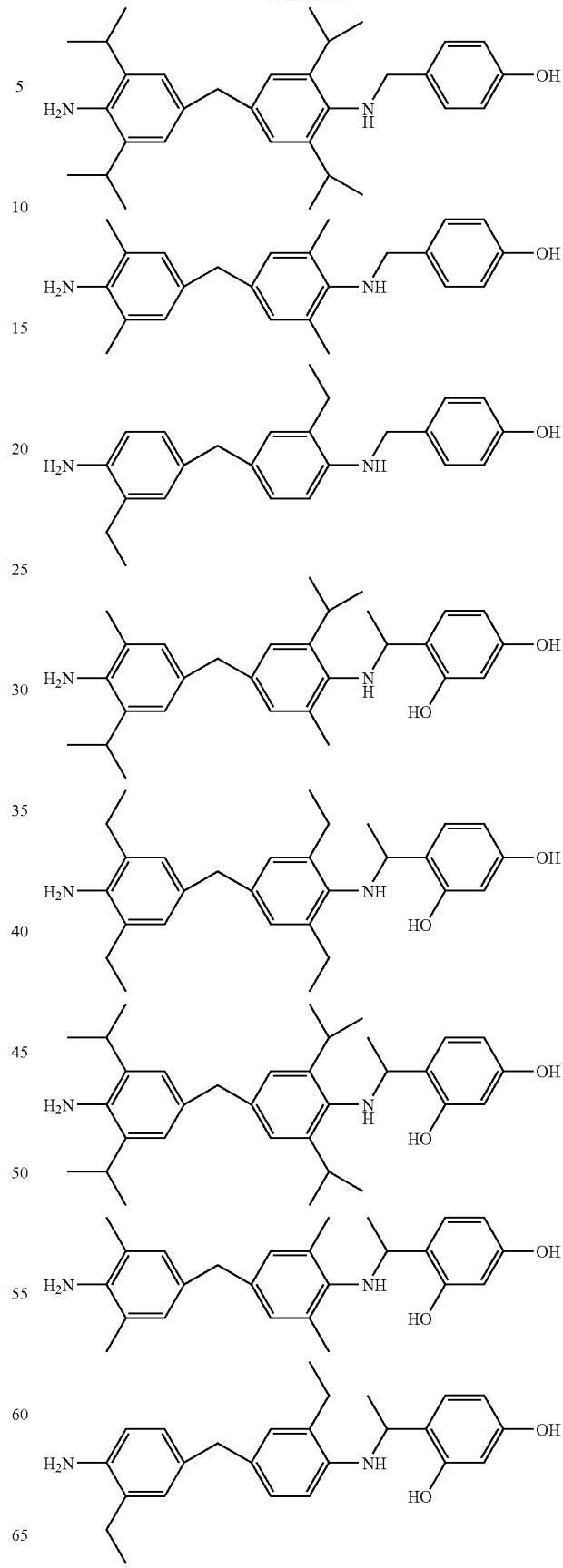

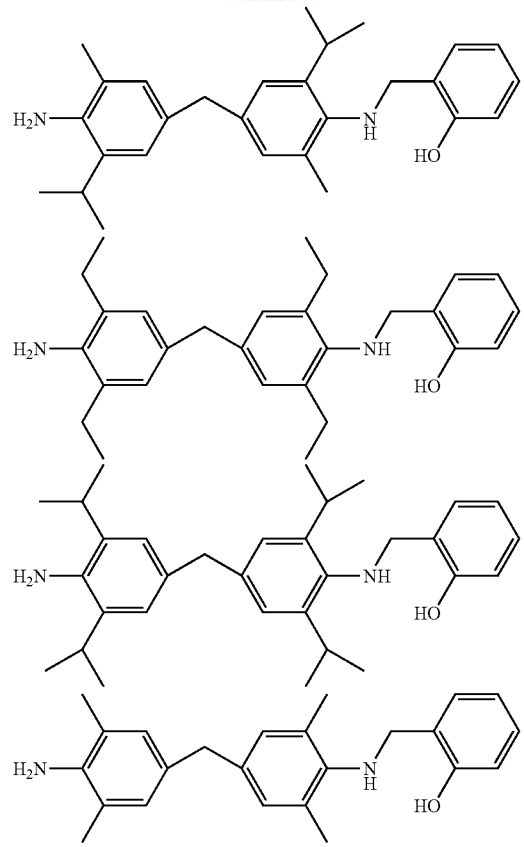
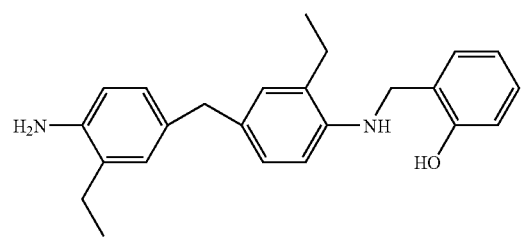
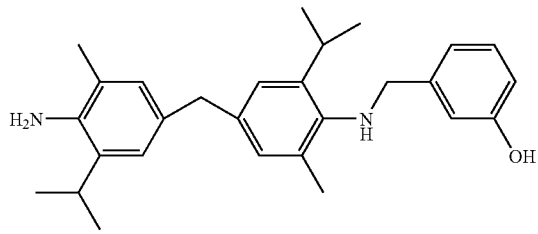
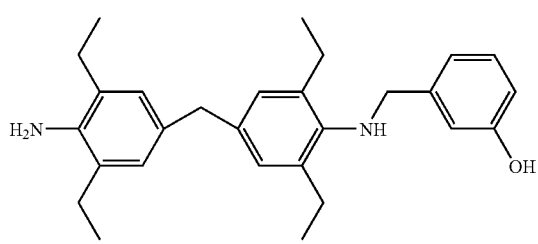
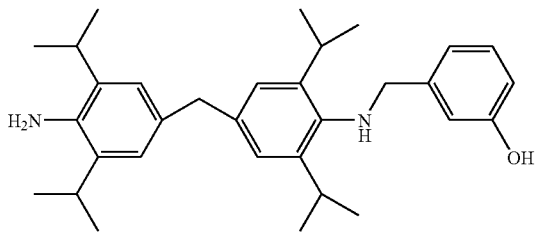
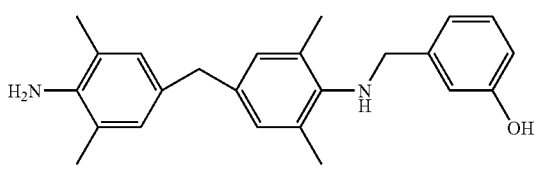
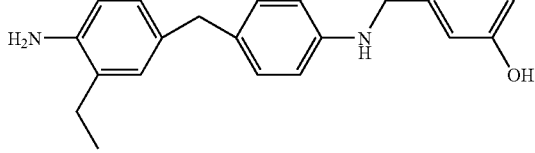
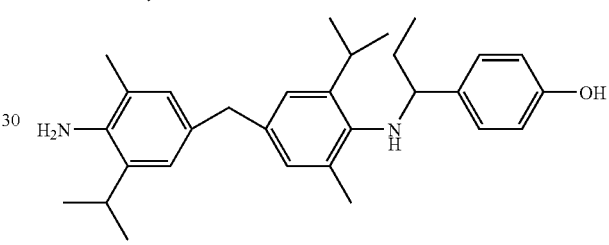
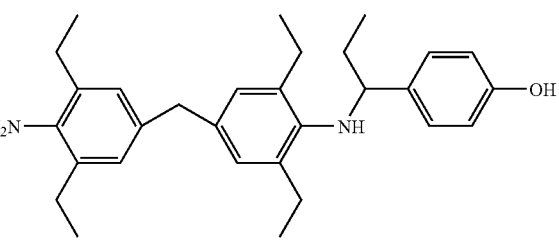
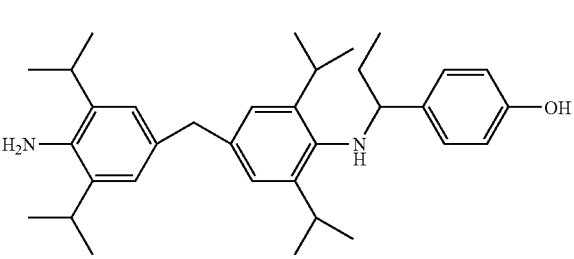
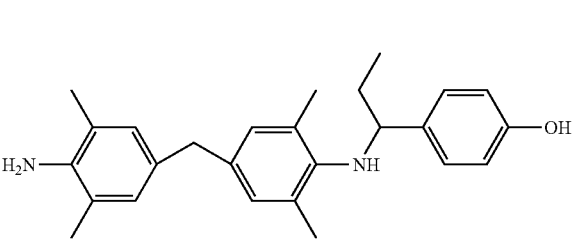

25
-continued
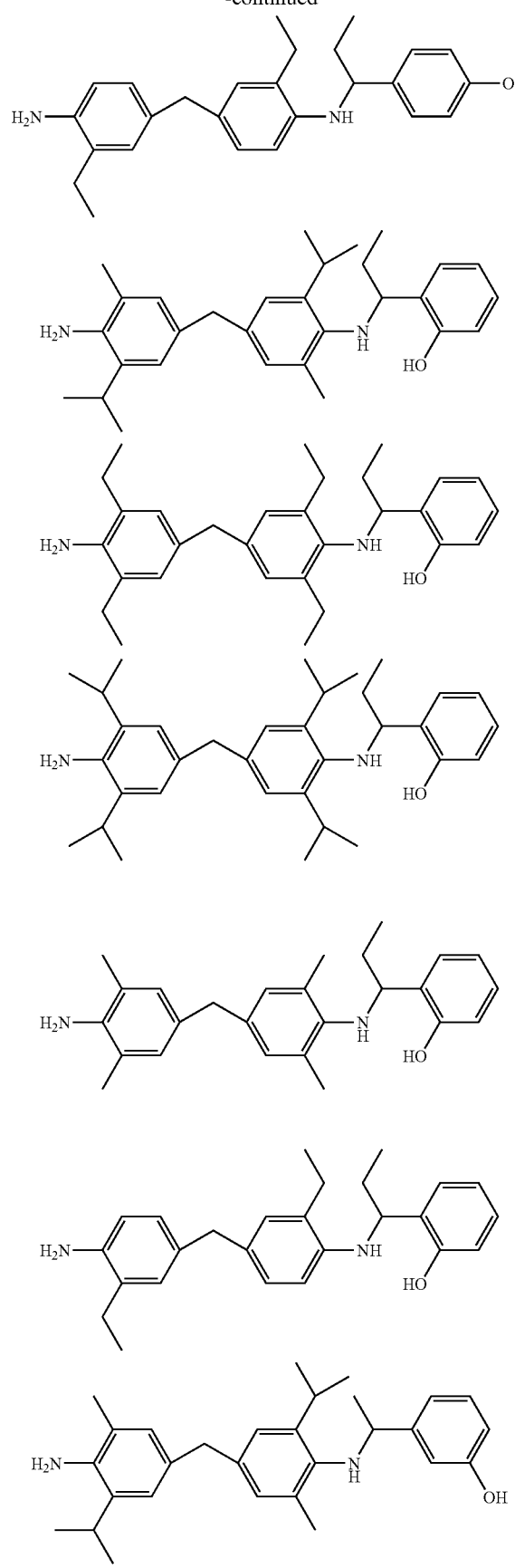
26
-continued
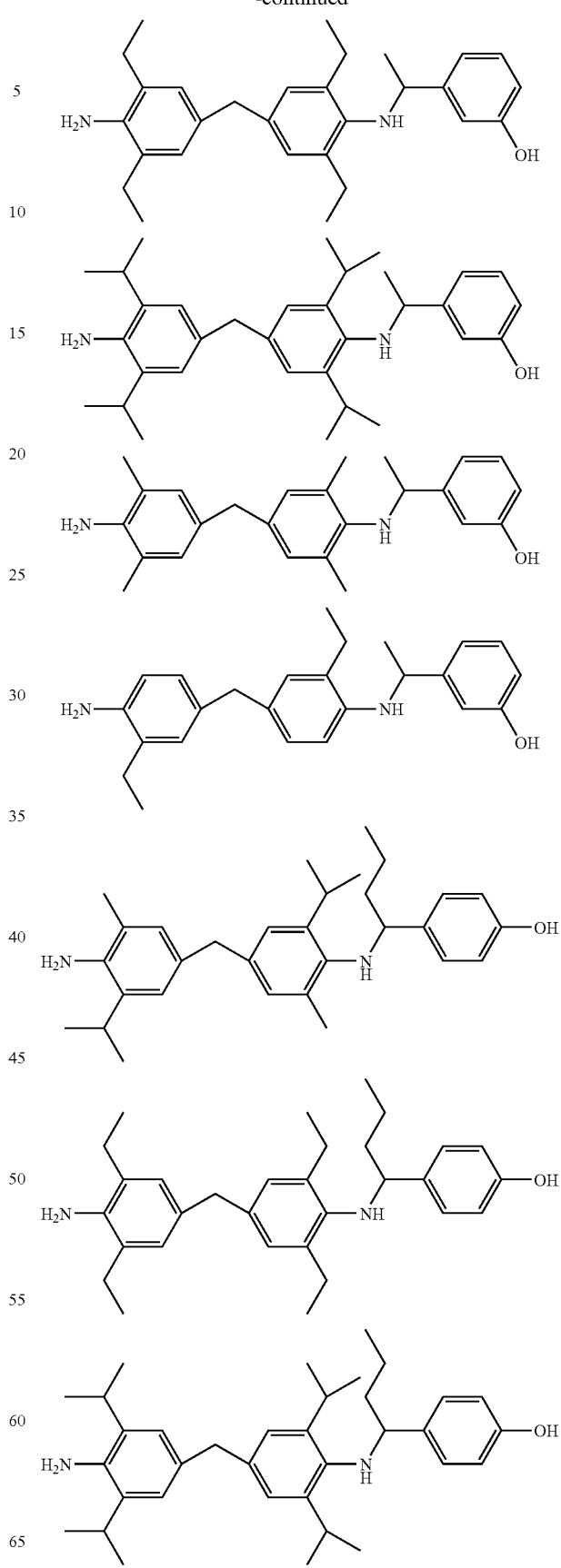

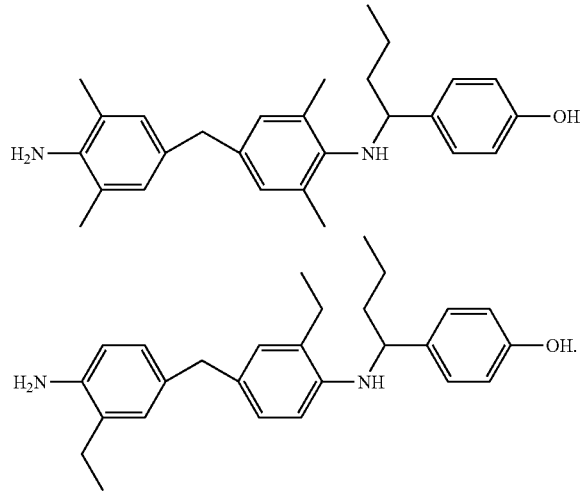

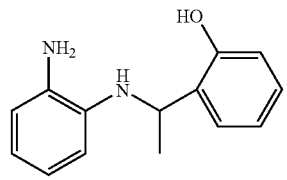

According to other embodiments of the present invention, it may be desirable to have amino-imine-phenol compounds that are sterically hindered. As mentioned above, the condensation of a diamine compound with an aromatic ketone or aldehyde is likely to generally produce a 1:2:1 statistical distribution of un-reacted diamine, an amine-phenol compound, and a diphenol, respectively.

The distribution however can, under certain circumstances, be skewed to yield predominantly only the amine-phenol hybrid product. Selective condensation to generate the amine-phenol hybrid is possible where either the diamine starting compound or the Schiff base condensation product are sterically hindered. An example of the selective condensation of a hindered diamine to yield an imine-linked hybrid amine-imine-phenol VI is shown by reaction scheme C:

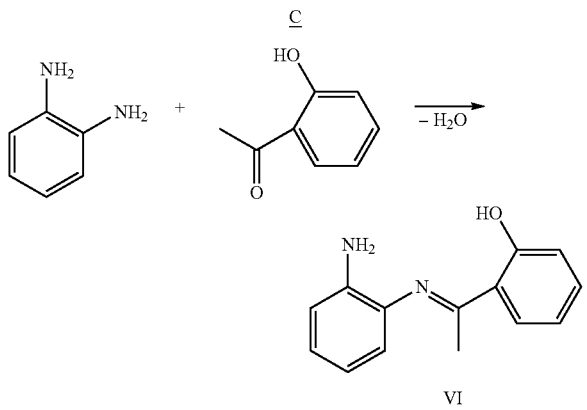

The reaction shown by the reaction scheme C can be generally carried out thermally (i.e., no catalyst is required), for example, at temperatures between about 125° C. and about 180° C. in the presence of an azeotropic solvent, and under an inert gas blanket. The reaction is monitored by the rate of water generated and collected in the trap. The reaction is generally complete after 2 to 36 hours of reflux.

The imine-linked amine-phenol hybrid VI that is produced according to reaction scheme C can also be hydrogenated according to the method illustrated by reaction scheme B, to yield the fully saturated compound VII:

An alternative approach to prepare hybrid amine-phenol epoxy curatives can be achieved through the direct condensation of benzyl alcohol derivatives with hindered phenols. A representative reaction scheme that can be used to prepare these compounds is shown by reaction scheme D:

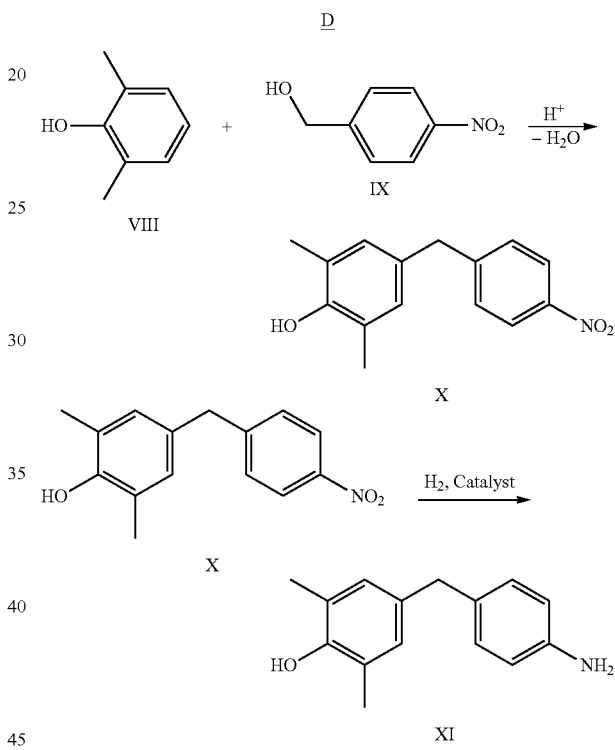

The first step in the reaction sequence shown by reaction scheme D benefits from select reactivity in both of the reagents used. The presence of the hydroxyl group in phenol activates the phenyl ring toward electrophilic substitution in the ortho- and para-positions. Since both of the ortho-positions in the exemplary phenol VIII are already substituted with alkyl groups, only the para-position, activated by the phenol function, is available for reaction. The presence of the nitro group on benzyl alcohol deactivates that phenyl ring and therefore auto condensation of the 4-nitrobenzyl alcohol IX with itself is not a significant potential side reaction. The condensation reaction between the substituted phenol VIII and the 4-nitrobenzyl alcohol IX can be catalyzed by either acid or base. Fewer side reactions are anticipated if acid catalysis is used.

The second step of the reaction sequence shown by reaction scheme D can be readily accomplished under mild conditions. The reduction of nitro groups in the intermediate X to amine functional groups in the final product XI is especially facile in the presence of hydrogen gas and a palladium catalyst. Other catalysts and/or hydrogen equivalents (e.g. potassium formate or phenyl hydrazine) may be used to effect this reduction.

Exemplary compounds that are contemplated in this invention, and produced by a reaction similar to that shown by the reaction scheme D include, but are not limited to, either of the following compounds:

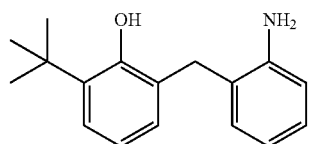

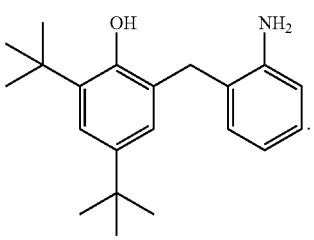

Other useful compounds that are contemplated in this invention and produced by the reaction similar to that shown by the reaction scheme D include, but are not limited to, any of the following compounds:

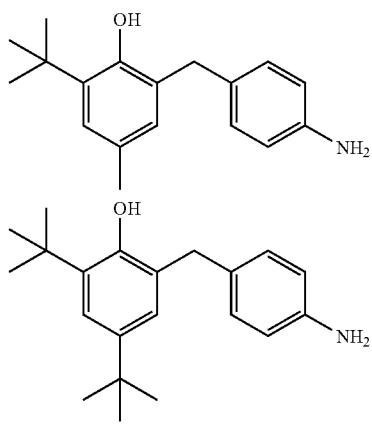

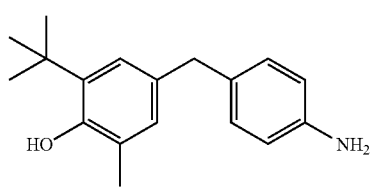

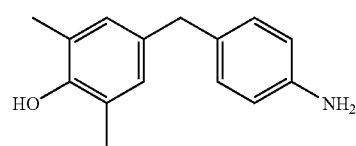

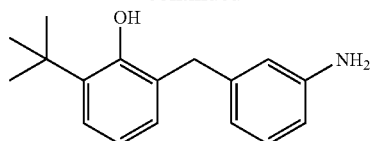

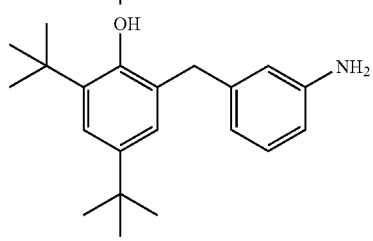

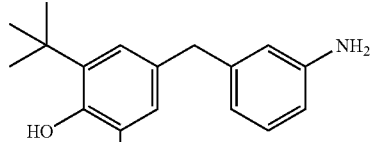

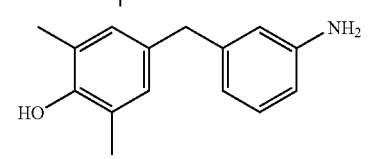

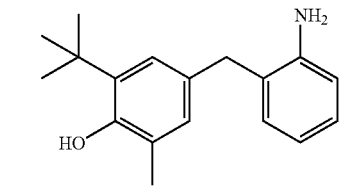

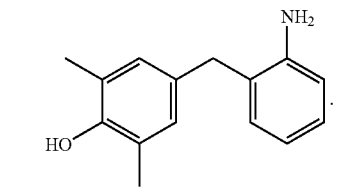

According to other embodiments of the present invention, a related condensation reaction could also be used to create another class of hybrid amine-phenol epoxy curatives. Nitro substituted benzaldehyde compounds XII can be condensed with hindered phenols XIII to yield dual functional molecules XIV. The intermediate nitro compounds XIV can then be hydrogenated to provide hybrid epoxy curatives XV. A generic representation of this reaction is shown by reaction scheme E:

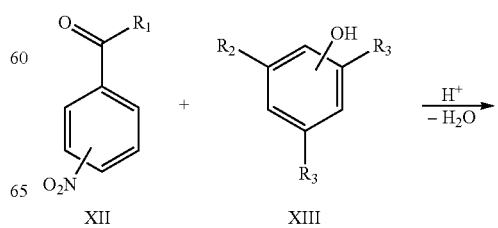

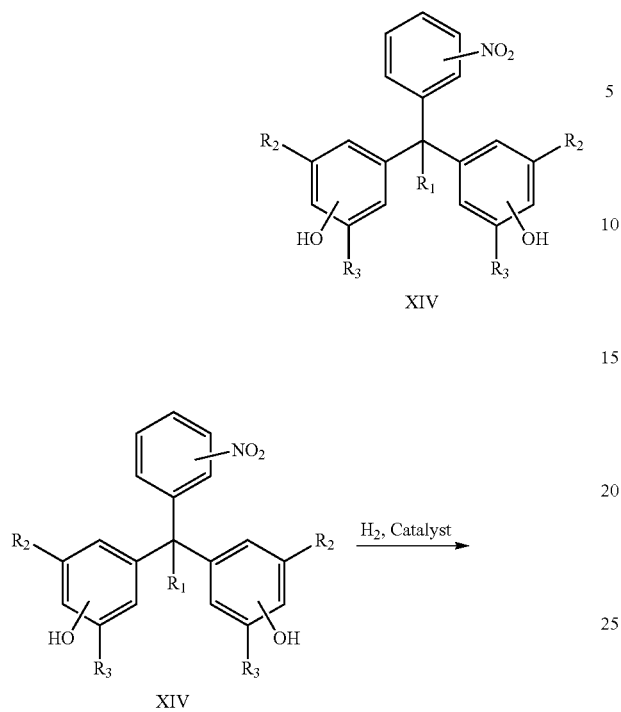

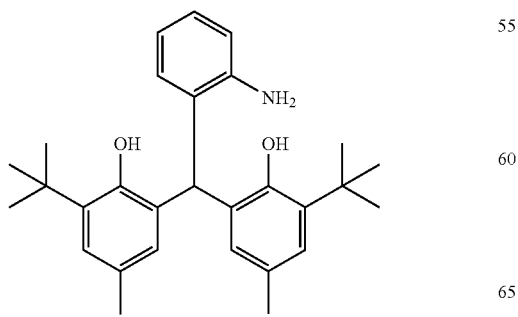

wherein $R_1$ is H, or lower alkyl and each of $R_2$ and $R_3$ is Cl, Br, F, or a lower alkyl.

Exemplary compounds that are contemplated in this invention, and produced by the reaction scheme E include, but are not limited to any of the following compounds:

Other useful compounds that are contemplated in this invention and produced by the reaction scheme E include, but are not limited to, any of the following compounds:

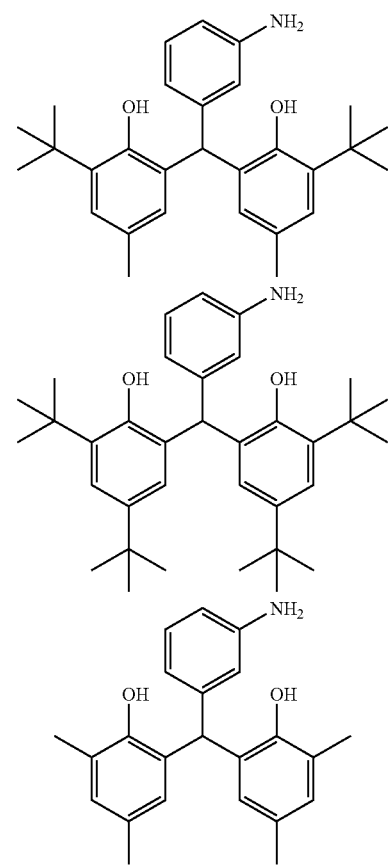

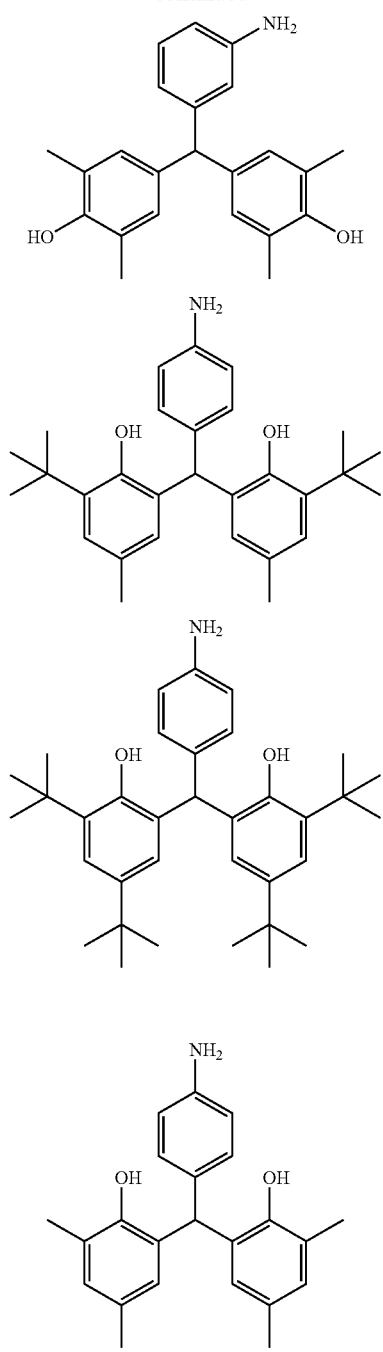
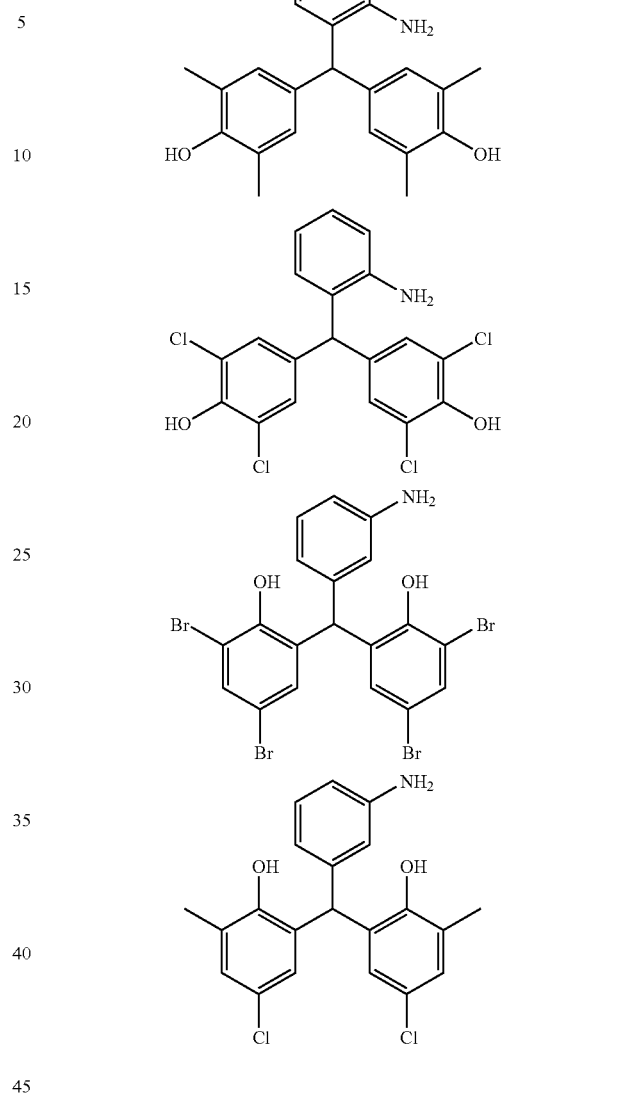
According to other embodiments of the present invention, ether linked hybrid amine-phenol curatives XVI can also be prepared by nucleophilic substitution of the halo substituent in a mono- or dinitrohalobenzene. A generic representation of this reaction is shown by reaction scheme F:
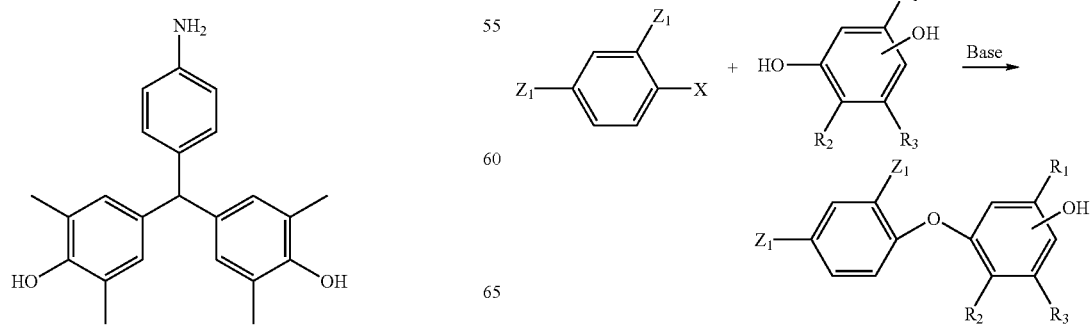

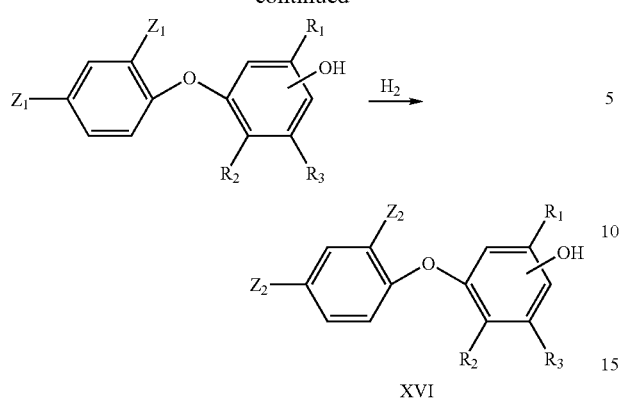

XVI wherein $Z_1$ is $NO_2$ or H, $Z_2$ is $NH_2$ or H, X is F, Cl, Br, or I; and each of $R_1$, $R_2$, and $R_3$ is a lower alkyl or H.

Exemplary compounds that are contemplated in this invention, and produced by the reaction scheme F include, but are not limited to any of the following compounds:

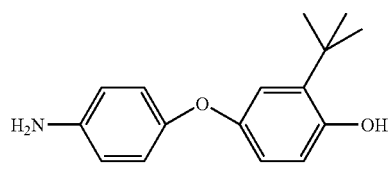

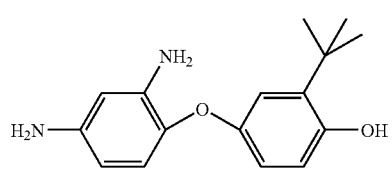

Other useful compounds that are contemplated in this invention and produced by the reaction scheme F include, but are not limited to, any of the following compounds:

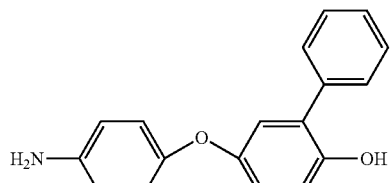

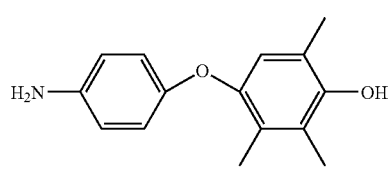

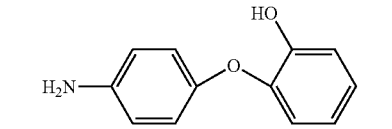

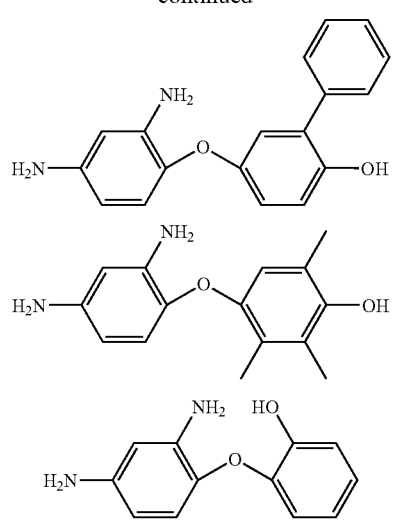

Related, ether-linked, hindered, hybrid amine-phenol compounds can be prepared where 2,3-dihydroxynapthalene or 2,2'-dihydroxybiphenyl, etc., are substituted for the dihydroxybenzene compounds shown on reaction scheme F.

According to other embodiments of the present invention, another class of hybrid epoxy curative compounds is contemplated. This class encompasses compounds that contain both aromatic amine and phenyl ester functional groups. Phenyl esters are, like their phenol parent compounds, capable of reacting with epoxies. They are, however, more latent in their reactions with epoxies than phenols. A wide variety of hybrid amine-phenyl ester curatives can be conveniently prepared in two, simple, high yield, reaction steps. A synthetic reaction sequence for one such hybrid amine-phenyl ester epoxy curative is exemplified as shown by reaction scheme G:

G

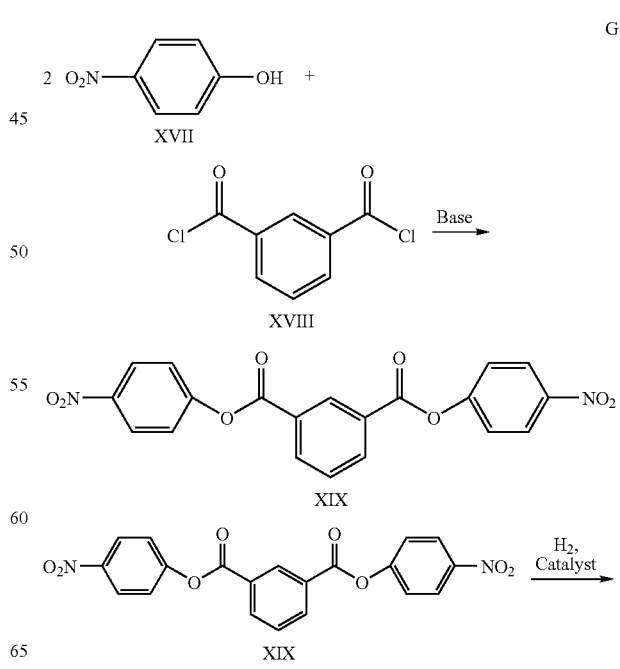

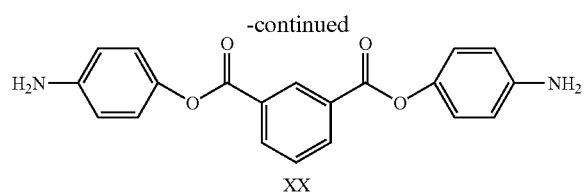

XX

The first step in this sequence is the reaction of a phenol XVII bearing one or more nitro substituents is condensed with a mono- or di-acid halide functional compound, such as the acid halide compound XVIII, to form phenyl-ester-bridged intermediates XIX followed by reduction (e.g., hydrogenation), to yield the final product XX. The acid halide compound XVIII itself may optionally also bear nitro substituents. It would also be possible to make these compounds directly from nitrophenols and benzoic acids through the use of a condensing agent such as N,N'-dicyclohexylcarbodiimide (DCC). A wide variety of hybrid amine-phenyl ester epoxy curative compounds can be prepared by this approach.

Exemplary compounds that are contemplated in this invention, and produced by the reaction scheme G include, but are not limited to, any of the following compounds:

Other useful compounds that are contemplated in this invention and produced by the reaction scheme G include, but are not limited to, any of the following compounds:

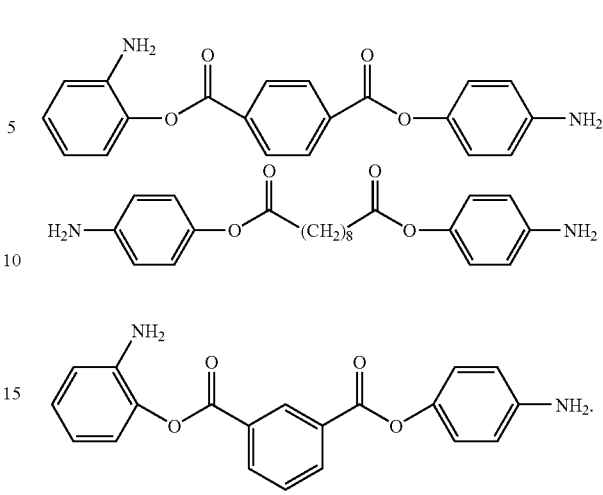

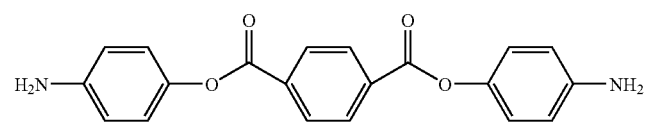

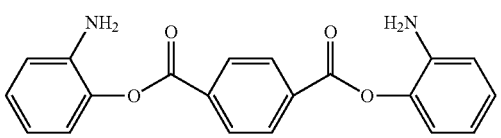

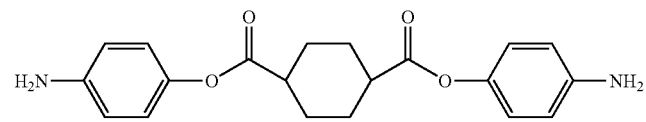

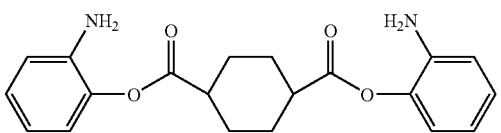

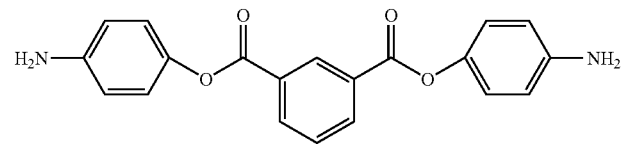

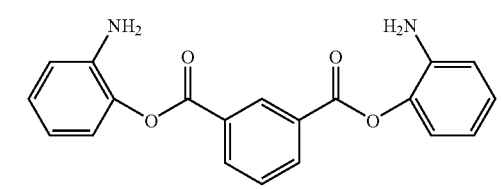

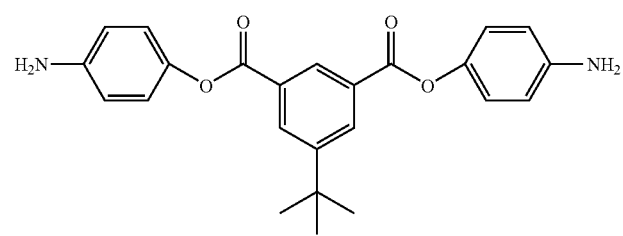

-continued
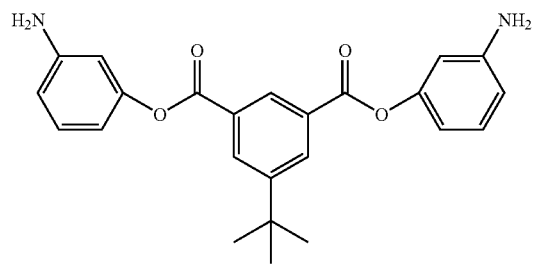
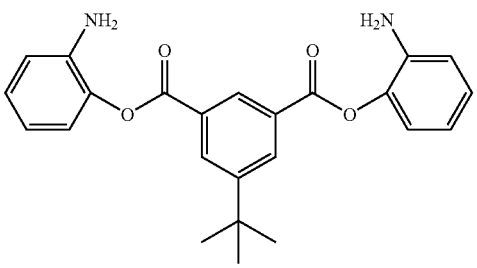
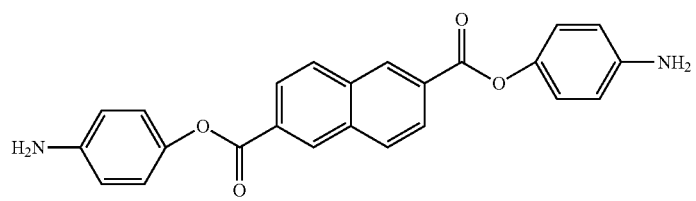
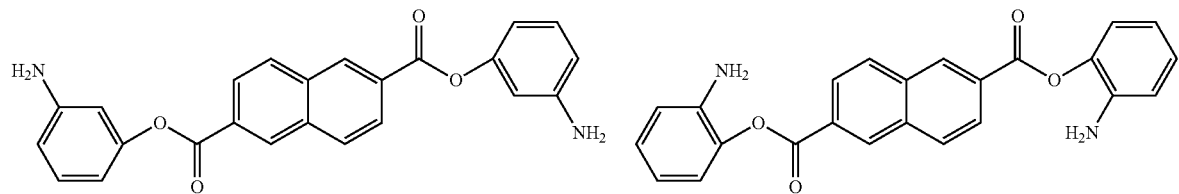
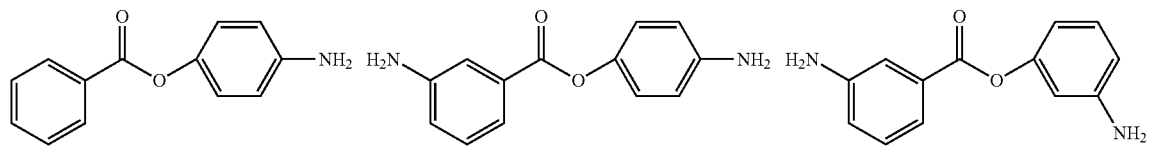
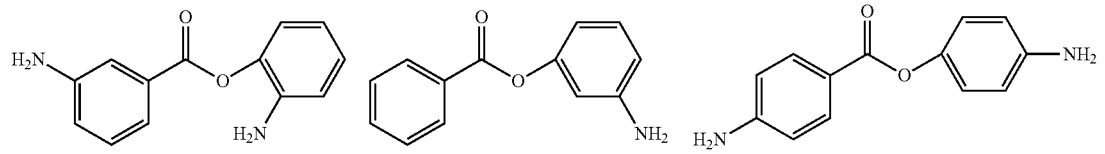
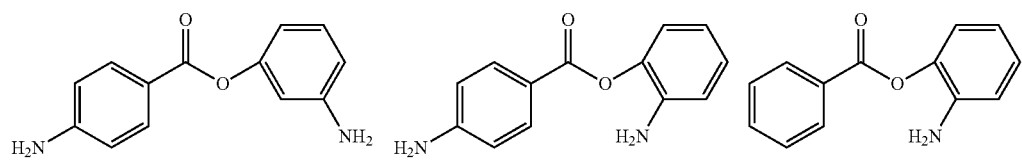
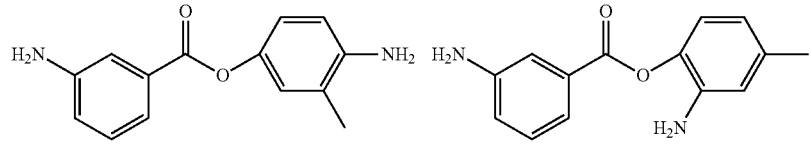
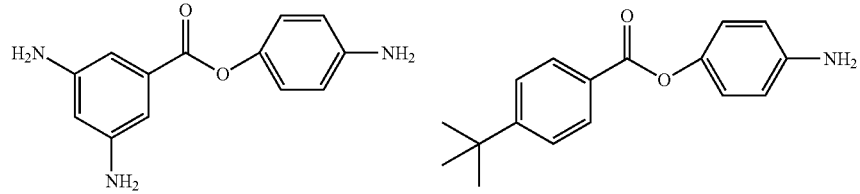
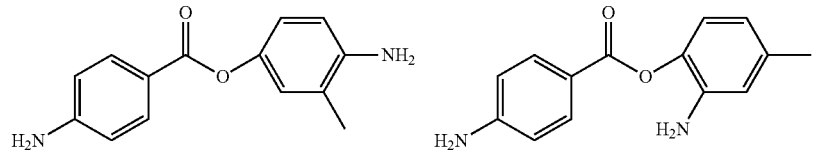

41
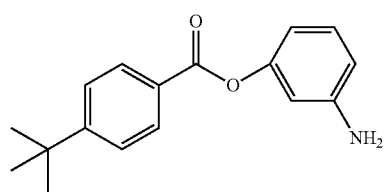
-continued
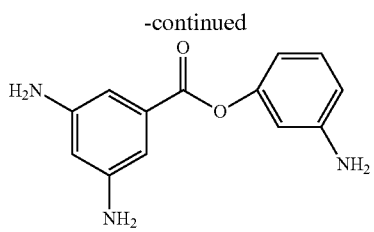
42
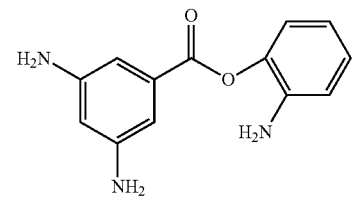
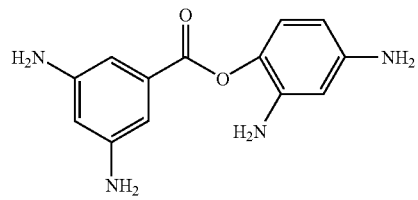
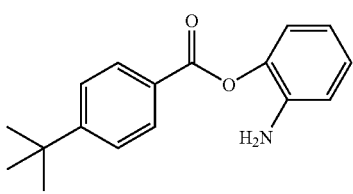
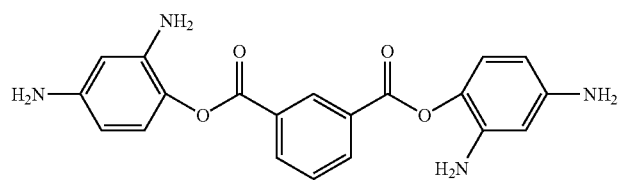
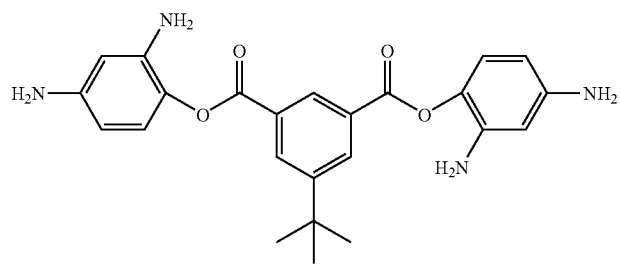
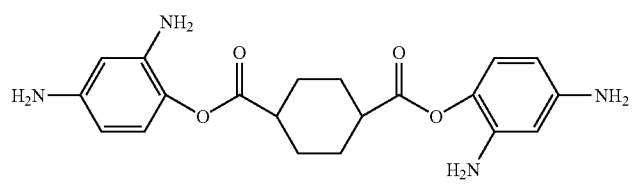
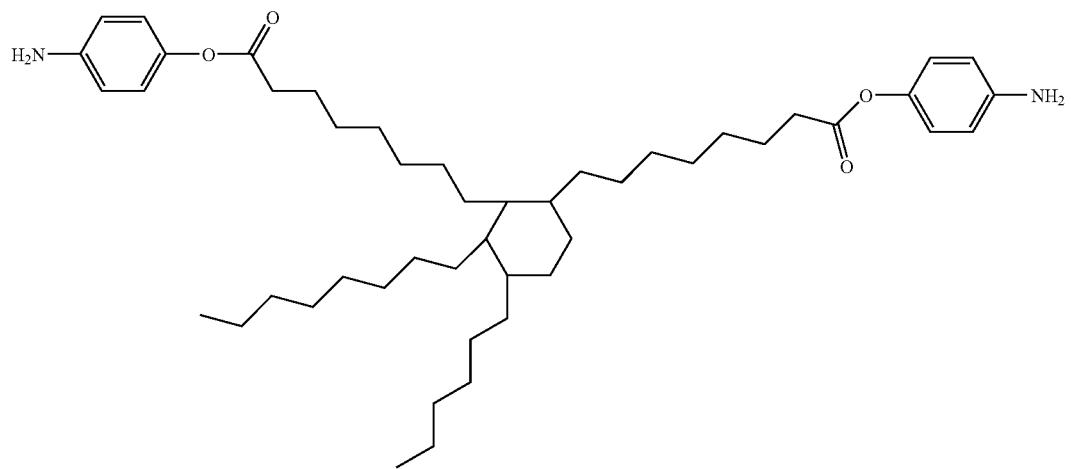

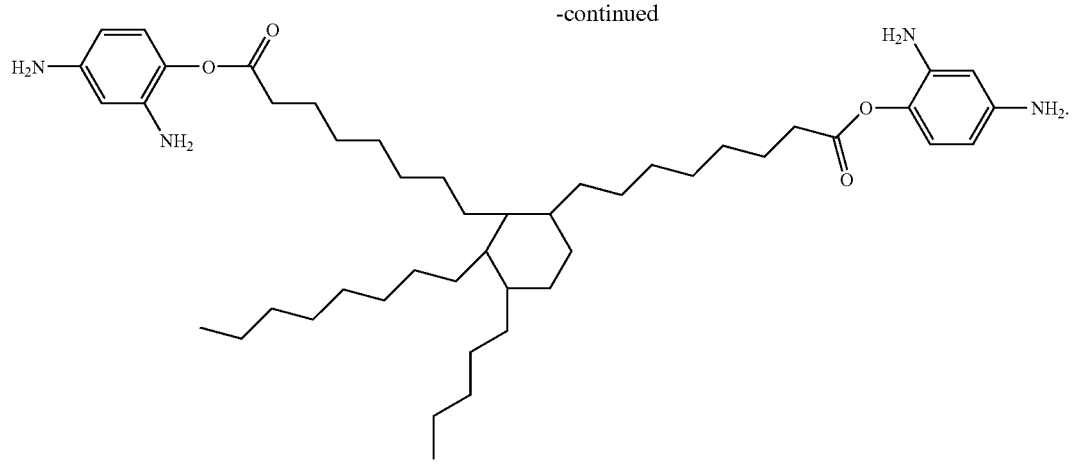

A similar series of amine-phenyl ester curatives can be prepared from the reaction of nitro-substituted benzoyl chlorides and bisphenols (or through the condensation of nitro-substituted benzoic acids and bisphenols in the presence of DCC) compounds followed by hydrogenation to convert the nitro functional groups into amines. Representative compounds include any of the following (designated as group XXI):

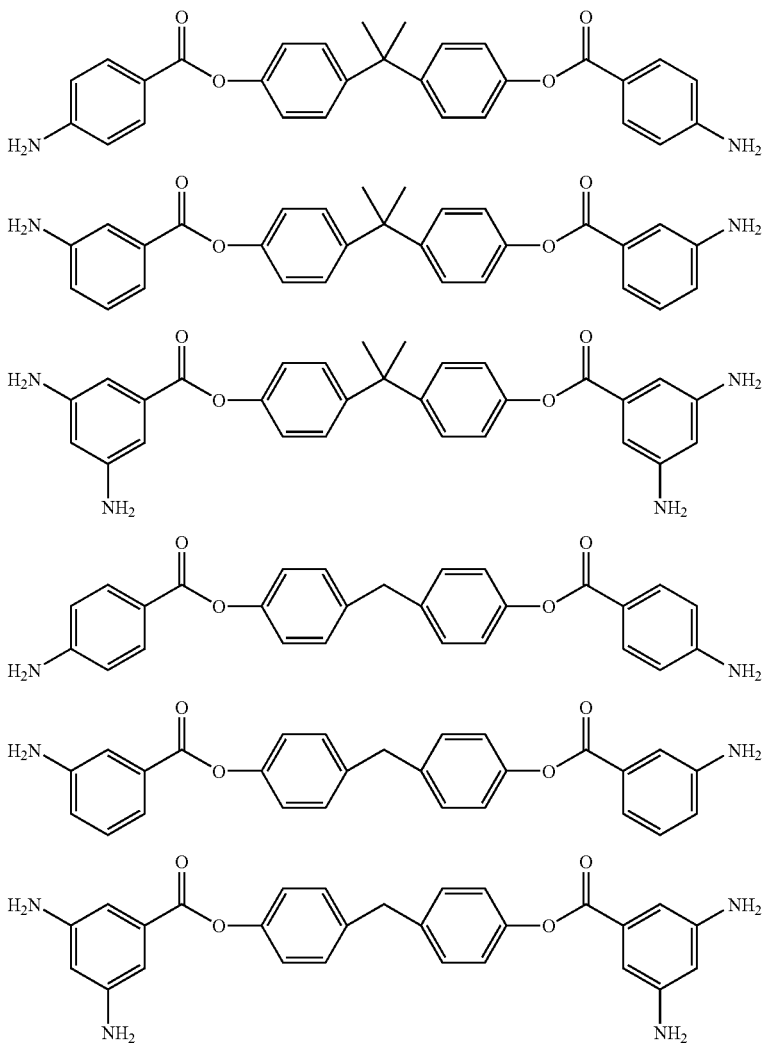

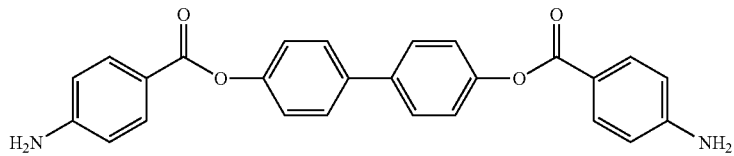
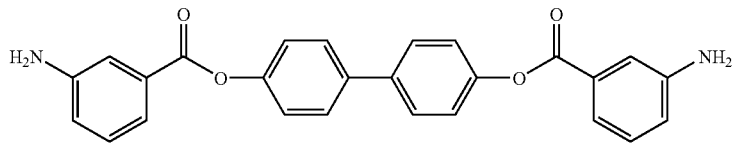
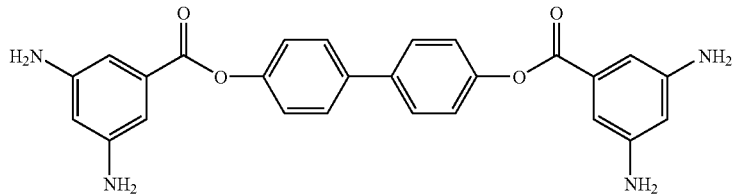
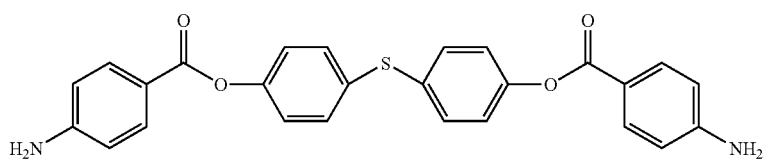
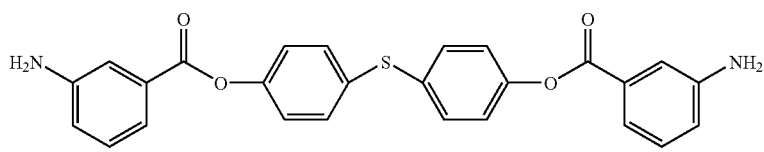
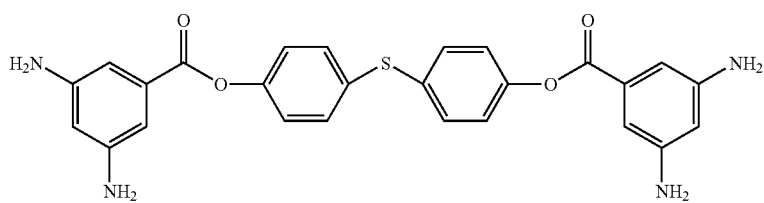
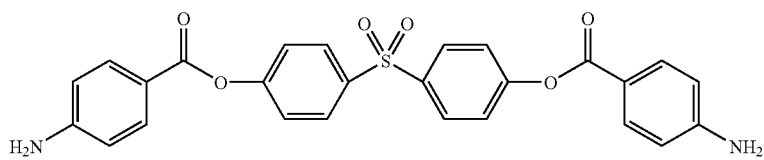
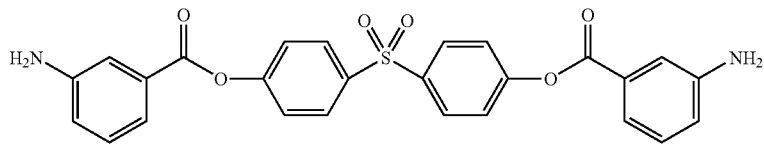
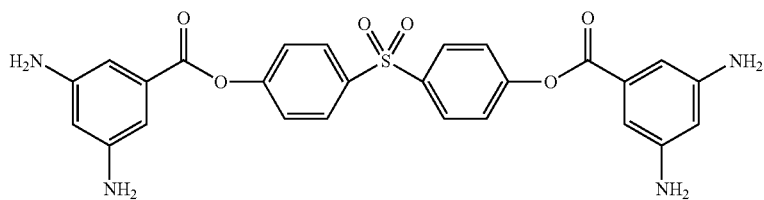
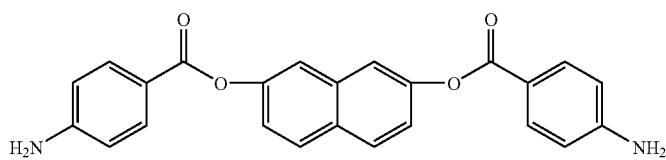

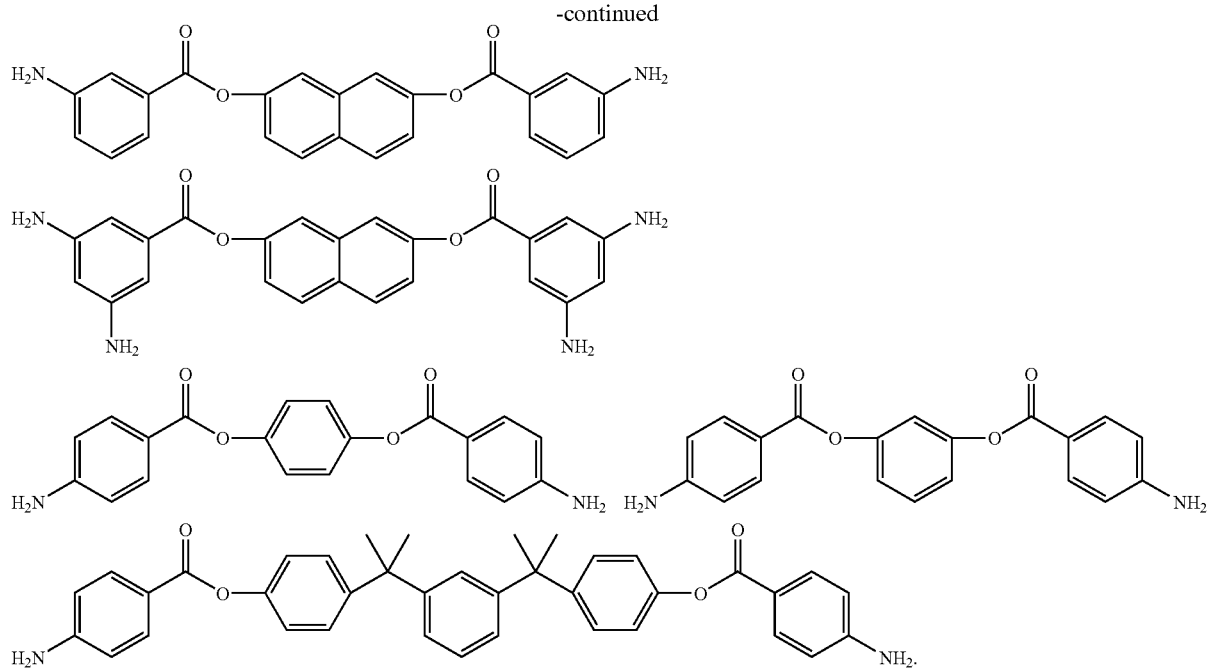

Amines can displace alcohols and phenols from their respective esters via aminolysis to form amides. Phenyl esters are inherently more reactive than esters of non-aromatic alcohols. It would be expected therefore that the amine-phenyl ester compounds would be inherently unstable and subject to both inter and intramolecular aminolysis. Surprisingly, it has been found that these compounds are more stable than expected and that the neat compounds do not appear to undergo significant aminolysis under about 200° C. It is unlikely, therefore, that aminolysis would be a serious side reaction that would compete with the epoxy ring opening function of these hybrid curatives.

Compositions Containing Compounds of the Present Invention

According to other embodiments of the present invention, compositions containing at least one epoxy resin and at least one compound according to any of the formulas III-VII, XV, or XVI, or compounds produced by the method generally outlined by the reaction schemes D or G, above, or compounds of group XXI, or any combination thereof. For example, compounds III-VII, XV, or XVI, or compounds produced by the method generally outlined by the reaction schemes D or G, or compounds of group XXI, or any combination thereof, may be combined with other materials and reagents, including other adhesives and/or resins to prepare epoxy adhesive compositions. Compounds III-VII, XV, or XVI, or compounds produced by the method generally outlined by the reaction schemes D or G, or compounds of group XXI, or any combination thereof, may be used as the sole curatives of an epoxy adhesive composition, or may be combined with other curatives or monomers, such as thermoset monomers, to make a fully formulated adhesive composition.

In certain embodiments of the invention, at least one of compounds III-VII, XV, or XVI, or compounds produced by the method generally outlined by the reaction schemes D or G, or compounds of group XXI, or any combination thereof, may be present in a composition, such as an adhesive composition, in an amount between about 0.1 weight percent (wt %) and about 99 wt %, based on the total weight of the composition. Typically, the composition may contain an amount of at least one of compounds III-VII, XV, or XVI, or compounds produced by the method generally outlined by the reaction schemes D or G, or compounds of group XXI, or any combination thereof, equal to at least about 0.5 wt %, or at least about 1 wt %, or at least 2 wt %, or at least 3 wt %, such as at least about 5 wt %, often at least about 10 wt %, frequently at least about 20 wt %, and in some embodiments at least about 40 wt % or at least about 50 wt % based on the total weight of the composition.

In another embodiment of the invention, the composition containing an epoxy resin and at least one of compounds III-VII, XV, or XVI, or compounds produced by the method generally outlined by the method generally outlined by reaction schemes D or G, or compounds of group XXI, or any combination thereof, may additionally include at least one co-monomer, which is typically present in an amount from 10 wt % to about 90 wt %, based on the total weight of the composition. In some aspects of the invention, the composition will contain an amount of the co-monomer equal to at least about 15 wt %, often at least about 20 wt %, frequently at least about 25 wt %, and in some embodiments at least about 30 wt % based on the total weight of the composition. Co-monomers suitable for use in such compositions according to the invention include, but are not limited to, acrylates, acrylamides, methacrylates, methacrylamides, cyanate esters, maleimides, vinyl ethers, vinyl esters, styrenic compounds, allyl functional compounds, other epoxies, other epoxy curatives, and olefins.

Curing Initiators. In certain embodiments, the present invention provides compositions, such as adhesive compositions, including at least one of compounds III-VII, XV, or XVI, or compounds produced by the method generally outlined by the reaction schemes D or G, or compounds of group XXI, or any combination thereof, a difunctional or polyfunctional epoxy monomer, and at least one curing initiator. The curing initiator is typically present in adhesive compositions of the invention at an amount from 0.1 wt % to about 5 wt %, based on total weight of the composition, and is typically a Lewis base, a Lewis acid, or salt thereof. In some embodiments, the curing initiator is present at least about 0.2 wt %, often at least about 0.5 wt %, frequently at least about 1 wt %, at in some embodiments at least about 2 wt %, based on total weight of the composition.

Compositions containing ethylenically unsaturated co-monomers may, in addition to the traditional epoxy catalysts, also contain one or more free-radical initiators. Free-radical initiators contemplated for use in the practice of the present invention typically decompose (i.e., have a half life in the range of about 10 hours) at temperatures in the range of about 70° C. up to 180° C. Exemplary free radical initiators contemplated for use in the practice of the present invention include peroxides (e.g. dicumyl peroxide, dibenzoyl peroxide, 2-butanone peroxide, tert-butyl perbenzoate, di-tert-butyl peroxide, 2,5-bis(tert-butylperoxy)-2,5-dimethylhexane, bis(tert-butyl peroxyisopropyl)benzene, and tert-butyl hydroperoxide), azo compounds (e.g., 2,2'-azobis(2-methyl-propanenitrile), 2,2'-azobis(2-methylbutanenitrile), and 1,1'-azobis(cyclohexanecarbonitrile)). Other free-radical initiators that will be well-known in the art may also be suitable for use in the compositions of the present invention.

Photoinitiators. Free radical initiators also include photo-initiators. For invention compositions that contain a photo-initiator, the curing process can be initiated, for example, by UV radiation. In one embodiment, the photoinitiator is present at a concentration of 0.1 wt % to 5 wt %, based on the total weight of the organic compounds in the composition (excluding any filler). In one embodiment, the photoinitiator comprises 0.5 wt % to 3.0 wt %, based on the total weight of the organic compounds in the composition. In other embodiments, the photoinitiator is present at least about 0.5 wt %, often at least about 1 wt %, frequently at least about 2 wt %, and in some embodiments at least about 3 wt %, based on the total weight of the organic compounds in the composition. Photoinitiators include benzoin derivatives, benzilketals, α,α-dialkoxyacetophenones, α-hydroxyalkylphenones, α-aminoalkylphenones, acylphosphine oxides, titanocene compounds, combinations of benzophenones and amines or Michler's ketone, and the like.

In some embodiments, both photoinitiation and thermal initiation may be desirable. For example, curing of a photo-initiator-containing adhesive can be started by UV irradiation, and in a later processing step, curing can be completed by the application of heat to accomplish a free-radical cure. Both UV and thermal initiators may therefore be added to the adhesive compositions of the invention.

Anionic Catalysts. The compounds of this invention can be cured with epoxy monomers in the presence of a cure catalyst. In some embodiments the initiator is an anionic catalyst. Examples of anionic initiators include Lewis bases such as tertiary amines and imidazoles. Specific examples include benzyldimethlamine, triethylamine, tripropylamine, pyridine, dimethylaminopyridine, dimethylethanolamine, diethylethanolamine, tributylamine, 2-methylimidazole, 2-undecylimidazole, 1-benzyl-2-methylimidazole, 1-cyanoethyl-2-methylimidazole, 1-cyanoethyl-2-phenylimidazole, 1-cyanoethyl-2-undecylimidazole, 1-cyanoethyl-2-ethyl-4-methylimidazole, 1-cyanoethyl-2-isopropylimidazole, 1-cyanoethyl-2-methylimidazole-trimellitate, 1-cyanoethyl-2-phenylimidazole-trimellitate, 1-cyanoethyl-2-ethyl-4-methylimidazole-trimellitate, 1-cyanoethyl-2-undecylimidazole-trimellitate, 2,4-diamino-6-(2'methylimidazolyl-(1')) ethyl-s-triazine, 2,4-diamino-6-(2'-ethyl-4'-methyl-imidazolyl-(1'))ethyl-s-triazine, 2,4-diamino-6-(2'-undecylimidazolyl-(1'))ethyl-s-triazine, 2-phenyl-4-methyl-5-hydroxymethylimidazole, 2-phenyl-4,5-dihydroxymethylimidazole, 1-cyanoethyl-2-phenyl-4,5-di (cyanoethoxymethyl)imidazole, 2-methylimidazole—isocyanuric acid addition compound, 2-phenylimidazole—isocyanuric acid addition compound, 2,4-diamino-6[2'-methylimidazolyl-(1)']ethyl-s-triazine isocyanurate adduct, 4,4'-methylene-bis-(2-ethyl-5-methylimidazole), and the like.

Cationic Catalysts. In other embodiments the initiator for the reaction between an epoxy and the curatives of this invention is a cationic catalyst. Cationic catalysts include Lewis acids such as zinc acrylate, zinc butarate, zinc 2-ethylhexanoate, zinc naphthanate, dibutyl tin laurate, and the like. Other specific examples of cationic catalysts include onium compounds. Specific examples include bis[4-(diphenylsulphonio)-phenyl]sulphide bis-hexafluorophosphate, bis[4-(di (2-hydroxyethyl)phenyl)sulphonio-phenyl]sulphide bis-hexafluorophosphate, bis[4-(di(4-(2-hydroxyethyl)phenyl) sulphonio) phenyl]sulphide bis-hexafluoroantimonate, ($\eta^5$-2,4-(cyclopentadienyl)[(1,2,3,4,5,6-$\eta$)-(methylethyl)-benzene]-iron(II) hexafluorophosphate, triarylsulphonium hexafluorophosphate, (tolylcumyl) iodonium tetrakis (pentafluorophenyl) borate, diaryl iodonium hexafluoroantimonate, and the like. In certain embodiments, the invention provides adhesive compositions including 0.5 wt % to about 98 wt % of at least one compound described herein, based on total weight of the composition; 10 wt % of about 90 wt % of at least one epoxy monomer; 0 to about 90 wt % of a conductive filler; 0.1 wt % to about 5 wt % of at least one curing initiator, based on total weight of the composition; and 0.1 wt % to about 4 wt %, of at least one coupling agent, based on total weight of the composition.

Additional Co-Curing Compounds. In certain aspects, the compositions, such as adhesive compositions of the invention include at least one additional compound that can co-cure with the epoxy resin(s) of the composition. The additional compound is typically present in an adhesive composition from about 10 wt % to about 90 wt % based on total weight of the composition. In such aspects, the composition will typically contain an amount of the co-curing compound equal to at least about 20 wt %, often at least about 30 wt %, frequently at least about 40 wt %, and in some embodiments at least about 50 wt % based on the total weight of the composition.

Such compounds include, for example, other epoxies (e.g. epoxies based on glydicyl ethers of alcohols, phenols, bisphenols, oligomeric phenolics, phenolic novolacs, cresolic novolacs, acrylates, methacrylates, maleimides, poly-phenol compounds (e.g. poly(4-hydroxystyrene)), anhydrides, dianhydrides, polyanhydrides such as styrene-maleic anhydride co-polymers, imides, carboxylic acids, dithiols, polythiols, phenol functional mono-maleimides, bismaleimides, polymaleimides, mono-itaconates, mono-maleates, mono-fumarates, acrylic acid, methacrylic acid, cyanate esters, vinyl ethers, vinyl esters, or phenol functional esters, ureas, amides, polyolefins (e.g. amine, carboxylic acid, hydroxy, and epoxy functional) siloxanes (e.g. epoxy, phenolic, carboxylic acid, or thiol functional), cyanoacrylates, allyl functional compounds and styrenic, as well as combinations thereof. In yet further embodiments, the invention provides cured adhesives prepared from compositions that include at least one epoxy resin and at least one of compounds III-VII, XV, or XVI, or compounds produced by the method generally outlined by the reaction schemes D or G, or compounds of group XXI, or any combination thereof.

Coupling Agents. In certain aspects, the adhesive compositions of the invention include at least one additional coupling agent. Exemplary coupling agents contemplated for use in the practice of the present invention include silicate esters, metal acrylate salts (e.g., aluminum methacrylate), titanates (e.g., titanium methacryloxyethylacetoacetate triisopropoxide), zirconates, or compounds that contain a copolymerizable group and a chelating ligand (e.g., phosphine, mercaptan, acetoacetate, and the like). In some embodiments, the coupling agent contains both a co-polymerizable function (e.g., vinyl, acrylate, methacrylate, epoxy, amine, thiol, anhydride, isocyanate, and phenol moieties) and a silicate ester function. The silicate ester portion of the coupling agent is capable of condensing with metal hydroxides present on the mineral surface of substrate, while the co-polymerizable function is capable of co-polymerizing with the other reactive components of invention adhesive compositions, such as die-attach pastes. In certain embodiments coupling agents contemplated for use in the practice of the invention are oligomeric silicate coupling agents such as poly(methoxyvinylsiloxane).

Adhesive Paste Compositions Containing Compounds of the Invention

In certain embodiments, the present invention provides adhesive compositions that are of various consistencies including, liquids, gels, pastes and solids. In one embodiment, the adhesive composition is a paste suitable for attaching an electronics die to a substrate (i.e., die-attach pastes). Die attach pastes of the invention are optimized for long-term reliability, rapid inline curing, long pot-life, viscosity and thixotropic control for fast automated dispensing and manufacturing.

In one embodiment, the present invention provides an adhesive composition that include 0.5 wt % to about 98 wt % based on total weight of the composition, of at least one of compounds III-VII, XV, or XVI, or compounds produced by the method generally outlined by the reaction schemes D or G, or compounds of group XXI, or any combination thereof; 0 to about 90 wt % of a filler, based on total weight of the composition; 0.1 wt % to about 5 wt % of at least one curing initiator, based on total weight of the composition; and 0.1 wt % to about 4 wt %, of at least one coupling agent, based on total weight of the composition.

B-Stageable Adhesives

In certain embodiments, the adhesive compositions and die attach pastes of the invention are B-stageable. The B-stageable adhesive can be dispensed onto a die or a substrate by a variety of methods well known to those skilled in the art. In some embodiments, the adhesive is cast from solution using techniques such as spin coating, spray coating, stencil printing, screen printing, and the like. This dual stage cure is especially attractive for applications were it is desirable to apply an adhesive in liquid form, cure the material to a non-tacky thermoplastic state, and then cure this B-staged adhesive in a final heating step to bond two or more parts together. Thus, this dual stage cure method of the invention is particularly advantageous for silicon wafer back coatings. The original adhesive mixture can be spin coated onto the back of a silicon wafer. The coating can then be B-staged with heat or light. The coated wafers can then be diced to yield individual microelectronic components, which may be thermally attached directly to a substrate, and/or stacked together. The thermal "tacking step" re-liquifies the adhesive coating and provides a thermoplastic bond between the parts. The final bonding step involves a thermal (or in some cases light-based) cure to cross-link the B-staged adhesive composition. This method of assembly is highly desirable because it is easier to manufacture (especially for stacked die) than a traditional liquid adhesive assembly, and is much less expensive and wasteful compared to film-based adhesive technology.

In certain embodiments, a solvent may be employed in the practice of the invention. For example, when the B-stageable adhesive is spin-coated onto a circular wafer, it is desirable to have an even coating throughout the entire wafer, i.e., the solvent or solvent system should have the ability to deliver the same amount of adhesive to each point on the wafer. Thus, the adhesive will be evenly coated throughout, i.e., there will be the same amount of material at the center of the wafer as at the edges. Ideally, the adhesive is "Newtonian", with a thixotropic slope of 1.0. In certain embodiments, the solvent or solvent systems used to dispense the B-stageable adhesive have slopes ranging from 1.0 to about 1.2.

In some instances, the B-stageable adhesive is dispensed onto the backside of a die that has been coated with a polyimide. Thus, the solvent or solvent system used to dispense the B-stageable adhesive should not have any deleterious effects on the polyimide coating. To achieve this goal, in certain embodiments, the solvent system will include a polar solvent in combination with a non-polar solvent. Typically, the polar solvent is suitable for use with at least one of compounds III-VII, XV, or XVI, or compounds produced by the method generally outlined by the reaction schemes D or G, or compounds of group XXI, or any combination thereof in B-stageable adhesives, and the non-polar solvent is a non-solvent for the compound(s) III-VII, XV, or XVI, or compounds produced by the method generally outlined by the reaction schemes D or G, or compounds of group XXI, or any combination thereof. In addition, the polar solvent typically has a lower boiling point than the non-polar solvent. Without wishing to be to be limited to a particular theory, it is believed that when the adhesive is dispensed and then B-staged, the lower boiling polar solvent escapes first, leaving behind only the nonpolar non-solvent, essentially precipitating the oligomer uniformly and leaving the polyimide film undamaged.

In some embodiments, the solvent or solvent system has a boiling point ranging from about 150° C. up to about 300° C. In some embodiments, the solvent system is a combination of dimethyl phthalate (DMP), NOPAR 13, and terpineol. In other embodiments, the solvent system is a 1:1 (by volume) ratio of terpineol and NOPAR 13.

In general, adhesive compositions such as die-attach pastes and B-stageable adhesive compositions of the invention, will cure within a temperature range of 80-220° C., and curing will be effected within a length of time of less than 1 minute up to about 60 minutes. The B-stageable adhesive composition may be pre-applied onto either a semiconductor die or onto a substrate. As will be understood by those skilled in the art, the time and temperature curing profile for each adhesive composition will vary, and different compositions can be designed to provide the curing profile that will be suited to a particular industrial manufacturing process.

Additional Compounds. In certain embodiments, the compositions of the invention, such as adhesives (including die-attach paste adhesives), may contain modifiers that lend additional flexibility and toughness to the resultant cured adhesive. Such modifiers may be any thermoset or thermoplastic material having a $T_g$ of 50° C. or less, and typically will be a polymeric material characterized by free rotation about the chemical bonds, the presence of ether groups, and the absence of ring structures. Suitable such modifiers include polyacrylates, poly(butadiene), polyTHF (polymerized tetrahydrofuran, also known as poly(1,4-butanediol)), CTBN (carboxy-terminated butadiene-acrylonitrile) rubber, and polypropylene glycol. When present, toughening compounds may be present in an amount up to about 15 percent by weight of at least one of compounds III-VII, XV, or XVI, or compounds produced by the method generally outlined by the reaction schemes D or G, or compounds of group XXI, or any combination thereof and any other monomer in the adhesive.

Inhibitors for free-radical cure may also be added to the adhesive compositions and die-attach pastes described herein to extend the useful shelf life. Examples of free-radical inhibitors include hindered phenols such as 2,6-di-tert-butyl-4-methylphenol; 2,6-di-tert-butyl-4-methoxyphenol; tert-butyl hydroquinone; tetrakis(methylene(3,5-di-tert-butyl-4-hydroxyhydrocinnamate))benzene; 2,2'-methylenebis(6-tert-butyl-p-cresol); and 1,3,5-trimethyl-2,4,6-tris(3',5'-di-tert-butyl-4-hydroxybenzyl)benzene. Other useful hydrogen-donating antioxidants such as derivatives of p-phenylenediamine and diphenylamine. It is also well know in the art that hydrogen-donating antioxidants may be synergistically combined with quinones and metal deactivators to make a very efficient inhibitor package. Examples of suitable quinones include benzoquinone, 2-tert butyl-1,4-benzoquinone; 2-phenyl-1,4-benzoquinone; naphthoquinone, and 2,5-dichloro-1,4-benzoquinone. Examples of metal deactivators include N,N'-bis(3,5-di-tert-butyl-4-hydroxyhydrocinnamoyl)hydrazine; oxalyl bis(benzylidenehydrazide); and N-phenyl-N'-(4-toluenesulfonyl)-p-phenylenediamine. Nitroxyl radical compounds such as TEMPO (2,2,6,6-tetramethyl-1-piperidinyloxy, free radical) are also effective as inhibitors at low concentrations. The total amount of antioxidant plus synergists typically falls in the range of 100 to 2000 ppm relative to the weight of total base resin. Other additives, such as adhesion promoters, in types and amounts known in the art, may also be added.

The adhesive compositions, such as die-attach paste adhesives, described herein will generally perform within the commercially acceptable ranges for die attach adhesives.

Commercially acceptable values for die shear for the adhesives on a 80×80 mil$^2$ silicon die are in the range of greater than or equal to 1 kg at room temperature, and greater than or equal to 0.5 kg at 260° C. Acceptable values for warpage for a 500×500 mil$^2$ die are in the range of less than or equal to 70 Nm at room temperature.

Fillers. In some embodiments, fillers are contemplated for use in the practice of the present invention, which can be electrically conductive and/or thermally conductive, and/or fillers which act primarily to modify the rheology of the resulting composition. Examples of suitable electrically conductive fillers that can be employed in the practice of the present invention include silver, nickel, copper, aluminum, palladium, gold, graphite, metal-coated graphite (e.g., nickel-coated graphite, copper-coated graphite, and the like), and the like. Examples of suitable thermally conductive fillers that can be employed in the practice of the present invention include graphite, aluminum nitride, silicon carbide, boron nitride, diamond dust, zinc oxide, alumina, and the like. Compounds which act primarily to modify rheology include polysiloxanes (such as polydimethyl siloxanes), silica, fumed silica, fumed alumina, fumed titanium dioxide, calcium carbonate and the like.

Underfill Compositions

During its normal service life, an electronic assembly is subjected to repeated cycles of widely varying temperature. Due to the differences in the coefficient of thermal expansion between the electronic component, the solder, and the substrate, thermal cycling can stress the components of the assembly and cause it to fail. To prevent the failure, the gap between the component and the substrate is filled with an underfill material to reinforce the solder material and to absorb some of the stress of the thermal cycling.

In practice, the underfill material is typically dispensed into the gap between and electronic component (such as a flip-chip) and the substrate by injecting the underfill along two or more sides of the component, with the underfill material flowing, usually by capillary action, to fill the gap. Alternatively, underfilling can be accomplished by backfilling the gap between the electronic component and the substrate through a hole in the substrate beneath the chip. In either method, the underfill material must be sufficiently fluid to permit filling very small gaps.

The requirements and preferences for underfills are well known in the art. Specifically, monomers for use in underfills should have high $T_g$ and low $\alpha_1$ CTE, important properties. A high $T_g$, preferably in the range of at least about 100-135° C., and a low modulus or $\alpha_1$, preferably lower than about 60-65 ppm/° C., are optimal for underfill compositions.

Epoxy compositions comprising at least one of compounds III-VII, XV, or XVI, or compounds produced by the method generally outlined by the reaction schemes D or G, or compounds of group XXI, or any combination thereof, are suitable for making underfill compositions. Thus, the present invention provides underfill compositions including at least one epoxy resin and at least one of compounds III-VII, XV, or XVI, or compounds produced by the method generally outlined by the reaction schemes D or G, or compounds of group XXI, or any combination thereof. Optionally, the underfill will also contain a fluxing agent and/or a filler.

Two prominent uses for underfill technology are in packages known in the industry as flip-chip, in which a chip is attached to a lead frame, and ball grid array, in which a package of one or more chips is attached to a printed wire board.

The underfill encapsulation may take place after the reflow of the metallic or polymeric interconnect, or it may take place simultaneously with the reflow. If underfill encapsulation takes place after reflow of the interconnect, a measured amount of underfill encapsulant material will be dispensed along one or more peripheral sides of the electronic assembly and capillary action within the component-to-substrate gap draws the material inward. The substrate may be preheated if needed to achieve the desired level of encapsulant viscosity for the optimum capillary action. After the gap is filled, additional underfill encapsulant may be dispensed along the complete assembly periphery to help reduce stress concentrations and prolong the fatigue life of the assembled structure. The underfill encapsulant is subsequently cured to reach its optimized final properties.

If underfill encapsulation is to take place simultaneously with reflow of the solder or polymeric interconnects, the underfill encapsulant, which can include a fluxing agent if solder is the interconnect material, first is applied to either the substrate or the component; then terminals on the component and substrate are aligned and contacted and the assembly heated to reflow the metallic or polymeric interconnect material. During this heating process, curing of the underfill encapsulant occurs simultaneously with reflow of the metallic or polymeric interconnect material.

A wide variety of acids are contemplated for use as the acidic fluxing agent. Typically, the acidic fluxing agent is a carboxylic acid such as, for example, 3-cyclohexene-1-carboxylic acid, 2-hexeneoic acid, 3-hexeneoic acid, 4-hexeneoic acid, acrylic acid, methacrylic acid, crotonic acid, vinyl acetic acid, tiglic acid, 3,3-dimethylacrylic acid, trans-2-pentenoic acid, 4-pentenoic acid, trans-2-methyl-2-pentenoic acid, 2,2-dimethyl-4-pentenoic acid, trans-2-hexenoic acid, trans-3-hexenoic acid, 2-ethyl-2-hexenoic acid, 6-heptenoic acid, 2-octenoic acid, (+/−)-citronellic acid, (R)-(+)-citronellic acid, (S)-(−)-citronellic acid, undecylenic acid, myristolic acid, palmitoleic acid, oleic acid, elaidic acid, cis-11-eicosenoic acid, erucic acid, nervonic acid, cis-3-chloroacrylic acid, trans-3-chloroacrylic acid, 2-bromoacrylic acid, 2-(trifluoromethyl)acrylic acid, 2-(bromomethyl)acrylic acid, 2-cyclopentene-1-acetic acid, (1R-trans)-2-(bromomethyl)-2-methyl-3-methylenecyclopentaneacetic acid, 2-acetamidoacrylic acid, 5-norbornene-2-carboxylic acid, 3-(phenylthio)acrylic acid, trans-styrylacetic acid, trans-cinnamic acid, alpha-methylcinnamic acid, alpha-phenylcinnamic acid, 2-(trifluoromethyl)cinnamic acid, 2-chlorocinnamic acid, 2-methoxycinnamic acid, cis-2-methoxycinnamic acid, 3-methoxycinnamic acid, 4-methylcinnamic acid, 4-methoxycinnamic acid, 2,5-dimethoxycinnamic acid, 3,4-(methylenedioxy)cinnamic acid, 2,4,5-trimethoxycinnamic acid, 3-methylindene-2-carboxylic acid, and trans-3-(4-methylbenzoyl)acrylic acid, oxalic acid, malonic acid, methylmalonic acid, ethylmalonic acid, butylmalonic acid, dimethylmalonic acid, diethylmalonic acid, succinic acid, methylsuccinic acid, 2,2-dimethylsuccinic acid, 2-ethyl-2-methylsuccinic acid, 2,3-dimethylsuccinic acid, meso-2,3-dimethylsuccinic acid, glutaric acid, (+/−)-2-methylglutaric acid, 3-methylglutaric acid, 2,2-dimethylglutaric acid, 2,4-dimethylglutaric acid, 3,3-dimethylglutaric acid, adipic acid, 3-methyladipic acid, (R)-(+)-3-methyladipic acid, 2,2,5,5-tetramethylhexanedioic acid, pimelic acid, suberic acid, azelaic acid, 1,10-decanedicarboxylic acid, sebacic acid, 1,11-undecanedicarboxylic acid, undecanedioic acid, 1,12-dodecanedicarboxylic acid, hexadecanedioic acid, docosanedioic acid, tetracosanedioic acid, tricarballylic acid, beta-methyltricarballylic acid, 1,2,3,4-butanetetracarboxylic acid, itaconic acid, maleic acid, fumaric acid, citraconic acid, mesaconic acid, trans-glutatonic acid, trans-beta-hydromuconic acid, trans-traumatic acid, trans, trans-muconic acid, cis-aconitic acid, trans aconitic acid, (+/−)-chlorosuccinic acid, (+/−)-bromosuccinic acid, meso-2,3-dibromosuccinic acid, hexa fluoroglutaric acid, perfluoroadipic acid hydrate, dibromo-maleic acid, DL-malic acid, D-malic acid, L-malic acid, (R)-(−)-citramalic acid, (S)-(+)-citramalic acid, (+/−)-2-isopropylmalic acid, 3-hydroxy-3-methylglutaric acid, ketomalonic acid monohydrate, DL-tartaric acid, L-tartaric acid, D-tartaric acid, mucic acid, citric acid, citric acid monohydrate, dihydroflumaric acid hydrate, tetrahydrofuran-2,3,4,5-tetracarboxylic acid, mercaptosuccinic acid, meso-2,3-dimercaptosuccinic acid, thiodiglycolic acid, 3,3'-thiodipropionic acid, 3,3'-dithiodipropionic acid, 3-carboxypropyl disulfide, (+/−)-2-(carboxymethylthio) succinic acid, 2,2',2'',2'''-[1,2-ethanediylidenetetrakis(thio)]-tetrakisacetic acid, nitromethanetrispropionic acid, oxalacetic acid, 2-ketoglutaric acid, 2-oxoadipic acid hydrate, 1,3-acetonedicarboxylic acid, 3-oxoadipic acid, 4-ketopimelic acid, 5-oxoazelaic acid, chelidonic acid, 1,1-cyclopropanedicarboxylic acid, 1,1-cyclobutanedicarboxylic acid, (+/−)-trans-1,2-cyclobutanedicarboxylic acid, trans-DL-1,2-cyclopentanedicarboxylic acid, 3,3-tetramethyleneglutaric acid, (1R, 3S)-(+)-camphoric acid, (1S,3R)-(−)-camphoric acid, (+/−)-cyclohexylsuccinic acid, 1,1-cyclohexanediacetic acid, (+/−)-trans-1,2-cyclohexanedicarboxylic acid, (+/−)-1,3-cyclohexanedicarboxylic acid, trans-1,2-cyclohexanedicarboxylic acid, 1,4-cyclohexanedicarboxylic acid, 1,3-adamantanedicarboxylic acid, 3-methylenecyclopropane-trans-1,2-dicarboxylic acid, cis-5-norbornene-endo-2,3-dicarboxylic acid, 1,3,5-cyclohexanetricarboxylic acid, 1,3,5-cyclohexanetricarboxylic acid, kemp's triacid, (1alpha.3alpha.5beta)-1,3,5-trimethyl-1,3,5-cyclohexanetricarboxylic acid, 1,2,3,4-cyclobutane-tetracarboxylic acid, and 1,2,3,4,5,6-cyclo-hexanehexacarboxylic acid monohydrate, phenylmalonic acid, benzylmalonic acid, phenylsuccinic acid, 3-phenylglutaric acid, 1,2-phenylenediacetic acid, homophthalic acid, 1,3-phenylenediacetic acid, 4-carboxyphenoxyacetic acid, 1,4-phenylenediacetic acid, 2,5-dihydroxy-1,4-benzenediacetic acid, 1,4-phenylenediacrylic acid, phthalic acid, isophthalic acid, 1,2,3-benzenetricarboxylic acid hydrate, terephthalic acid, 1,2,4-benzenetricarboxylic acid, 1,2,4,5-benzenetetracarboxylic acid, mellitic acid, 3-(carboxymethylaminomethyl)-4-hydroxybenzoic acid, 4-methylphthalic acid, 2-bromoterephthalic acid, 4-bromoisophthalic acid, 4-hydroxyisophthalic acid, 4-nitrophthalic acid, nitrophthalic acid, 1,4-phenylenedipropionic acid, 5-tert-butylisophthalic acid, 5-hydroxyisophthalic acid, 5-nitroisophthalic acid, 5-(4-carboxy-2-nitrophenoxy)-isophthalic acid, diphenic acid, 4,4'-biphenyldicarboxylic acid, 5,5'dithiobis(2-nitrobenzoic acid), 4-[4-(2-carboxybenozoyl)phenyl]-butyric acid, pamoic acid, 1,4-naphthalenedicarboxylic acid, 2,3-naphthalenedicarboxylic acid, 2,6-naphthalenedicarboxylic acid, 1,4,5,8-naphthalene-tetracarboxylic acid hydrate, 2,7-di-tert-butyl-9,9-dimethyl-4,5-xanthenedicarboxylic acid, and the like.

A particularly useful carboxylic acid for the preparation of the latent fluxing agents of the present invention is DIACID 1550®, a monocyclic $C_{21}$ dicarboxylic acid product derived from tall oil fatty acids, commercially available from Westvaco Corporation.

Mold Compounds and Compositions

In the electronics industry, a semiconductor chip or die mounted to a "package" substrate may be overmolded with a mold compound to provide a level of protection from environmental effects such as moisture and contaminants.

In terms of reliability performance, various properties of mold compositions materials are generally considered important. The properties desirable for mold compositions are known in the art. See, for example, U.S. Pat. Nos. 7,294,915, 6,512,031, and 6,429,238. These include low CTE, low modulus, adhesion, and high fracture toughness of the cured resin. A high $T_g$, preferably in the range of at least about 100-135° C., and a low modulus or $\alpha_1$, preferably lower than about 60-65 ppm/° C., are optimal for mold compositions. See, for example, U.S. Pat. Nos. 6,512,031 and 5,834,848. A typical overmolding process places a solid or semi-solid molding compound over the chip using a mold press. The package is then transferred through a heated mold that causes the molding compound to flow and encapsulate the chip.

Mold compositions are highly filled compositions. They are typically filled with silica. This high filler loading is critical to their performance in terms of CTE (coefficient of thermal expansion), flame retardance, and thermal conductivity.

The compounds of the present invention have properties desirable of mold compounds. Specifically, compositions including at least one epoxy resin and at least one of compounds III-VII, XV, or XVI, or compounds produced by the method generally outlined by the reaction schemes D or G, or compounds of group XXI, or any combination thereof, have a high $T_g$ and low $\alpha_1$ CTE. A high $T_g$, such as in the range of at least about 100-135° C., and a low modulus or $\alpha_1$, such as lower than about 60-65 ppm/° C., are optimal for mold compositions. Thus, the present invention provides mold compositions containing compositions including at least one epoxy resin and at least one of compounds III-VII, XV, or XVI, or compounds produced by the method generally outlined by the reaction schemes D or G, or compounds of group XXI, or any combination thereof.

Assemblies

The present invention also provides assemblies of components adhered together by the above-described adhesive compositions (e.g., B-stageable adhesives and die-attach pastes) of the invention. Thus, for example, assemblies comprising a first article adhered to a second article by a cured aliquot of an adhesive composition containing at least one epoxy resin and compositions including at least one epoxy resin and at least one of compounds III-VII, XV, or XVI, or compounds produced by the method generally outlined by the reaction schemes D or G, or compounds of group XXI, or any combination thereof, are provided. Articles contemplated for assembly employing invention compositions include electronic components such as dies, memory devices (e.g. as flash memory devices), ASIC devices, microprocessors, and other microelectronic components. Assemblies also include microelectronic devices, such as copper lead frames, Alloy 42 lead frames, silicon dice, gallium arsenide dice, and germanium dice, that are adhered to a substrate by a cured aliquot of the above-described adhesive compositions Additional embodiments of the invention include adhesively bonded structures containing at least one epoxy resin and compositions including at least one epoxy resin and at least one of compounds III-VII, XV, or XVI, or compounds produced by the method generally outlined by the reaction schemes D or G, or compounds of group XXI, or any combination thereof. Non-limiting examples of the adhesively bonded structures include electronic components bonded to a substrate, and circuit components bonded to printed wire boards. In other embodiments of the invention, articles of manufactures can be comprised substantially of a cured amount of the composition described herein, such as an industrial, marine, automotive, airline, aerospace, sporting goods, medical or dental article. Such articles of manufacture can also include fillers, extenders, pigments and/or reinforcing materials along with the compositions disclosed herein.

Conditions suitable to cure invention die attach paste adhesives include subjecting the above-described assembly to a temperature of less than about 200° C. for about 0.5 up to 2 minutes. This rapid, short duration heating can be accomplished in a variety of ways, e.g., with an in-line heated rail, a belt furnace, or the like. Optionally, the material can be oven cured at 150-220° C.

In other embodiments the invention provides methods for attaching a semiconductor die to a substrate. Such methods can be performed, for example, by (a) applying a die-attach adhesive composition described herein to the substrate and/or the semiconductor die, (b) bringing the substrate and the die into contact to form an assembly, such that the substrate and the die are separated only by the die-attach adhesive composition applied in step (a), and (c) subjecting the assembly to conditions sufficient to cure the die-attach paste, thereby attaching the semiconductor die to the substrate.

Methods of Using Compositions Containing Compounds of the Invention

According to the present invention, methods for adhesively attaching a first article to a second article are provided. Such methods can be performed, for example, by a) applying an adhesive composition of the invention to the first article, the second article or both the first and second articles; b) contacting the first article and the second article, where the first article and the second article are separated only by the adhesive composition applied in step a); and c) curing the adhesive composition applied in step a), thereby adhesively attaching the first article to the second article.

In one aspect of this method, the first and second articles are a semiconductor die and a substrate, respectively. Typically, according to this aspect the adhesive is a die attach paste. The method can include the steps of applying the adhesive composition (e.g. die attach paste) to the substrate, the semiconductor die, or both the substrate and the semiconductor die; b) melting the adhesive composition applied in step a); c) contacting the semiconductor device and the substrate, where the die and substrate are separated only by the adhesive composition applied in step a); and d) curing the adhesive composition applied in step a), thereby adhesively attaching the semiconductor device to the substrate. Applying the adhesive composition can include spin-coating, spray coating, stencil printing, screen printing and other methods well known in the art.

It will be understood those of skill in the art that using the compounds and methods of the present invention, it is possible to prepare adhesives having a wide range of cross-link density by the judicious choice and amounts of at least one epoxy resin and at least one of compounds III-VII, XV, or XVI, or compounds produced by the method generally outlined by the reaction schemes D or G, or compounds of group XXI, or any combination thereof, that are present in a composition being used. The strength and elasticity of individual adhesives can be tailored to a particular end-use application.

In still further embodiments, the invention provides B-stageable type methods for adhesively attaching a semiconductor die to a substrate. Such methods can be performed, for example, by applying an invention adhesive composition to the substrate, the semiconductor device or both the substrate and the semiconductor device; melting the applied adhesive composition applied; (c) contacting the semiconductor device and the substrate, such that the die and substrate are separated only by the applied adhesive composition; and curing the applied adhesive composition, thereby attaching the semiconductor device to the substrate.

Properties of Adhesives Containing Compounds of the Invention

Advantageously, the compounds of the invention can impart many properties that are desirable in an adhesive. Historically, the large majority of integrated circuits have been mounted on printed circuit boards using lead-based soldering. However, the demand for lead-free materials is increasing year by year, and electrically conductive adhesives are seen as an environmentally-friendly alternative.

Adhesiveness. To fully replace lead-based solders, adhesives in the microelectronic industry, adhesives must address the need for signal and power distribution, heat dissipation (i.e., cooling) while at the same time having and maintaining high adhesiveness. Conductive adhesives, for example, typically have conductive fillers dispersed in a polymer matrix.

The polymer matrix, when cured, provides the mechanical adhesion, but can interfere with conductivity and increase electrical resistance.

EXAMPLES

The invention will now be further described with reference to by the following illustrative, non-limiting examples.

Example 1

Synthesis of Compound 1

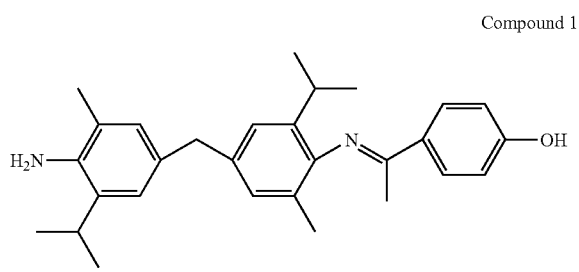

Compound 1

Methylene-1,1-bis(2-isopropyl-6-methylaniline) (Lonzacur®, 31.1 g, 100 mmol available from Lonza Group of Switzerland), 4'-hydroxyacetophenone (13.6 g, 100 mmol), and toluene (50 ml) were added to a 2-neck, 500 ml flask. A Dean-Stark trap, condenser and bubbler were attached to one neck of the flask and a temperature controller probe was inserted into the other. The mixture was stirred and heated to 165° C. under an argon blanket. Approximately 35 ml of toluene originally charged into the flask was removed to permit the temperature to attain the 165° C. target reflux temperature. A total of 1.75 ml of water was collected (theory=1.8 ml) after twenty-four hours of reflux. The toluene was removed via rotary evaporation at 95-100° C. The product was then placed in an oven set at 130° C. for 4 hours to remove the last traces of residual solvent. The reaction yielded 42.3 g (98.8%) of a deep red, glassy product. The compound was subjected to thermogravimetric analysis (TGA). The retained weight at 200° C. (TGA ramp rate=10° C./min., air purge) was 99.1% and the decomposition onset was at 309° C. An FTIR spectrum of this compound included prominent absorptions at 2960, 1409, 1630, 1601, 1515, 1442, 1362, 1275, 1169, and 837 wavenumbers.

Example 2

Synthesis of Compound 2

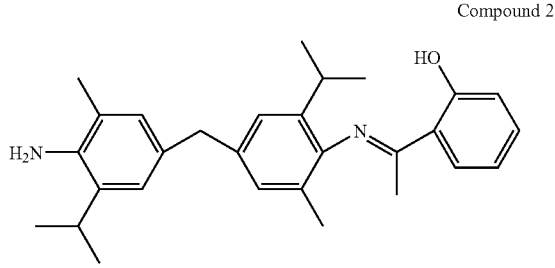

Compound 2

Methylene-1,1-bis(2-isopropyl-6-methylaniline) (Lonzacur®, 62.1 g, 200 mmol available from Lonza Group of Switzerland), 2'-hydroxyacetophenone (27.2 g, 200 mmol), and toluene (50 ml) were charged into a 2-neck, 500 ml flask. A Dean-Stark trap, condenser, and bubbler were attached to one neck and a temperature controller probe was attached to the other. An argon blanket was placed over the reaction mixture. The mixture was stirred and refluxed at 165° C. Approximately 35 ml of toluene were removed for the temperature to attain the 165° C. target reflux temperature. A total of 3.6 ml (equal to theory) of water was collected after 29.5 hours of reflux. The toluene was removed via rotary evaporation and air sparge, followed by vacuum oven treatment. The reaction yielded 85.6 g (99.9%) of an amber, glassy solid. The compound was subjected to TGA. The retained weight at 200° C. (TGA ramp rate=10° C./min., air purge) was 99.7% and the decomposition onset was at 317° C. The infrared spectrum of this compound included prominent absorptions at 2959, 1712, 1613, 1574, 1442, 1364, 1304, 1250, 1204, 1159, 841, and 752 wavenumbers.

Example 3

Synthesis of Compound 3

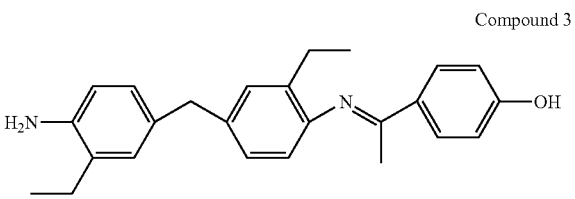

Compound 3

4,4'-Diamino-3,3'-diethyl diphenyl methane (25.4 g, 100 mmol), 4'-hydroxyacetophenone (13.6 g, 100 mmol), and toluene (50 ml) were added to a 2-neck flask. A Dean-Stark trap, condenser and bubbler were added. The mixture was refluxed for 13.3 hrs at 165° C. under an argon blanket. Approximately 35 ml of toluene were removed to drive the reflux temperature up to 165° C. A total of 1.8 ml of water (equivalent to theory) was collected. The toluene was removed via rotary evaporation, air sparge, and finally drying the product in an oven at 120° C. The product recovered consisted of 37.1 g (99.6%) of a reddish brown, glassy solid. The compound was subjected to thermogravimetric analysis (TGA). The retained weight at 200° C. (TGA ramp rate=10° C./min., air purge) was 99.2% and the decomposition onset was at 273° C. The infrared spectrum of this compound included prominent absorptions at 2963, 1704, 1600, 1503, 1439, 1364, 1273, 1169, and 836 wavenumbers.

Example 4

Synthesis of Compound 4

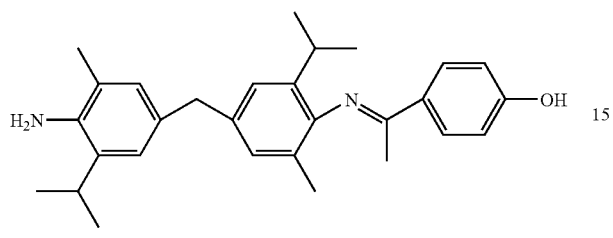

Compound 4

Methylene-1,1-bis(2-isopropyl-6-methylaniline) (Lonzacur®, 36.1 g, 116 mmol available from Lonza Group of Switzerland), 4'-hydroxyacetophenone (13.6 g, 100 mmol), and toluene (50 ml) were added to a 2-neck flask. A dean stark trap, condenser, and bubbler were added to one neck and a temperature probe to the other. The mixture was stirred and heated to 165° C. under an Argon blanket. Approximately 35 ml of toluene were removed for the temperature to stay at 165° C. A total of 1.8 ml of water (equivalent to theory) was collected after 27.8 hours of reflux. The toluene was removed via an argon sparge at 165° C. The product was recovered as 46.5 g (97.4%) of a dark red glassy solid. The compound was subjected to TGA. The retained weight at 200° C. (TGA ramp rate=10° C./min., air purge) was 99.6% and the decomposition onset was at 276° C. The infrared spectrum included prominent absorptions at 2958, 1710, 1602, 1514, 1442, 1362, 1272, 1205, 1170, and 837 wavenumbers.

Example 5

Synthesis of Compound 5

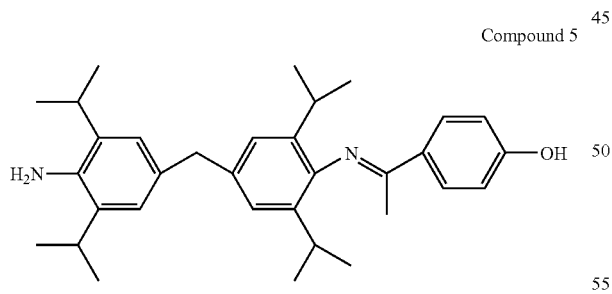

Compound 5

Methylene-1,1-bis(2,6-diisopropylaniline) (Lonzacur®, 36.7 g, 100 mmol available from Lonza Group of Switzerland), 4'-hydroxyacetophenone (13.6 g, 100 mmol), and toluene (50 ml) were added to a 2-neck, 500 ml flask. A Dean-Stark trap, condenser, and bubbler were added to one neck and a temperature controller probe to the other. The mixture was stirred and refluxed at 165° C. under an Argon blanket. A total of 1.9 ml of water (theory=1.8 ml) was collected after 22 hours of reflux. The toluene was removed via an argon sparge at 165° C. for 2 hours. The product was a pink solid that weighed 47.1 g (97.2%). The compound was subjected to TGA. The retained weight at 200° C. (TGA ramp rate=10° C./min., air purge) was 99.9% and the decomposition onset was at 294° C. Infrared spectrum included significant absorptions at 2957, 2870, 1711, 1599, 1514, 1463, 1363, 1289, 1169, 1107, 949, 885, 837, and 767 wavenumbers.

Example 6

Synthesis of Compound 6

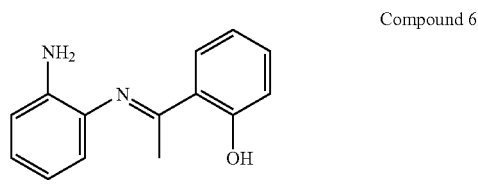

Compound 6

A 2-neck, 250 ml flask was charged with 1,2-Phenylenediamine (21.6 g, 200 mmol), 2-hydroxyacetophenone (27.2 g, 200 mmol), and toluene (50 ml). A condenser, Dean-Stark trap, and bubbler were attached to one neck, and a temperature controller probe to the other. An argon blanket was placed over the flask contents. The mixture was refluxed at 140° C. for 75 minutes and 3.6 ml of water (equivalent to theory) was collected. The toluene was removed via an argon sparge at 140° C. for 25 minutes. The product was recovered at first as a reddish-brown taffy-like solid. It was recrystallized in isopropyl alcohol (with a volume of IPA in ml equal to five-times its own the weight in grams). The solids were recovered via a Buchner funnel. The recrystallized product consisted of golden crystals. The compound was subjected to TGA. The retained weight at 100° C. (TGA ramp rate=10° C./min., air purge) was 99.9% and the decomposition onset was at 204° C. A DSC (differential scanning calorimeter) run was conducted (ramp rate=2° C./min., air purge) on a sample of the recrystallized product. The melting point was observed to occur with an onset of 106.2° C. and a minima at 108.3° C. Infrared spectrum included significant absorptions at 3458, 3350, 1709, 1616, 1564, 1490, 1447, 1365, 1302, 1255, 1193, 1155, 1036, 970, 852, 834, and 757 wavenumbers.

Example 7

Synthesis of Compound 7

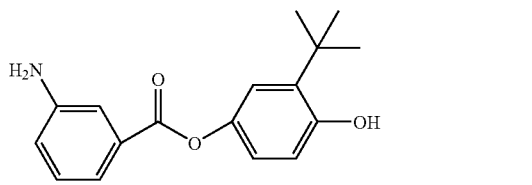

Compound 7

Triethylamine (5.6 g, 55 mmol), tert-butylhydroquinone (8.3 g, 50 mmol), and toluene (75 ml) were stirred in a 250 ml flask. A solution of 3-nitrobenzoyl chloride (9.3 g, 50 mmol) in 50 ml toluene was dripped in at room temperature. The addition caused the mixture to turn brownish black. A precipitate also formed. The mixture was heated to dissolve the solids. The mixture stirred overnight at room temperature.

The solution was washed with deionized water (3×25 ml) then with brine (25 ml). The product crashed out while it was still in the separatory funnel. The product was filtered with a Buchner funnel and rinsed with toluene. The resulting powdery solid was placed in a beaker and mixed with water. The solids were collected using a Buchner funnel and which were then rinsed with additional water. The compound was then placed into an oven set at 75° C. until completely dry. A total 8.6 g of an off white powder was collected. A DSC run was conducted (ramp rate=2° C./min., air purge) on a sample of this nitro compound intermediate. The melting point was observed to occur with an onset of 173.9° C. and a minima at 177.1° C. An FTIR was run on the nitro intermediate compound and it was found to have major absorptions at 3469, 2961, 1722, 1617, 1532, 1422, 1350, 1251, 1175, 1113, 1064, 926, 786, and 716 wavenumbers.

The nitro compound obtained as described above (8.6 g, 27.3 mmol), isopropyl alcohol (100 ml), and 10% palladium on carbon (100 mg) were added to a 3-neck, 500 ml flask. The solution was heated to 80° C. to fully dissolve the intermediate compound. A balloon filled with hydrogen gas was attached to the flask. The mixture stirred at 80° C. for 45 minutes. The temperature was then turned down to 35° C. The mixture stirred overnight at this temperature. An FTIR run showed the disappearance of the characteristic absorptions in the nitro intermediate (1532 and 1350 cm$^{-1}$). The solution was filtered over silica (10 g). The isopropyl alcohol was removed via rotary evaporation and air sparge. The final product yielded 7.6 g (97.7% of theory based on the nitro compound intermediate) of an orange waxy solid. The compound was subjected to thermogravimetric analysis (TGA). The retained weight at 100° C. (TGA ramp rate=10° C./min., air purge) was 99.8% and the decomposition onset was at 282.1° C. A DSC run was conducted (ramp rate=2° C./min., air purge) on a sample of the amine compound. The melting point was observed to occur with an onset of 117.1° C. and a minima at 124.8° C. An FTIR was run on the final amine product and it was found to have major absorptions at 3384, 2963, 1718, 1622, 1506, 1422, 1293, 1180, 1132, 1062, 996, 941, 883, 805, 748, and 679 wavenumbers.

Example 8

Epoxy Compositions

Test compositions were prepared using curative compounds 1-7 from Examples 1-7, as provided above. The test compositions were prepared by blending a one to one equivalent mixture of each of the curatives with bisphenol F diglycidyl ether (D.E.R.™ 354, The Dow Chemical Company, Midland Mich.). The mixtures were catalyzed with one weight percent of Curezol 2P4MZ (Air Products and Chemicals, Inc. Allentown, Pa.) imidazole catalyst. Approximately 45 milligrams of each of the catalyzed mixtures were then cured in a DSC cell at a ramp rate of 10° C. per minute. This first DSC run was used to evaluate the cure onset, peak maximum, and energy. The cell was then cooled to about 5° C. and another DSC was run, at a ramp rate of 5° C. per minute, on each of the cured samples to determine the glass transition temperature. The glass transition temperature was determined from the inflection point in the DSC curve. The results of these thermal tests are summarized in Table 1.

TABLE 1

DSC Test Results for Invention Curatives and Bisphenol F Diglycidyl Ether

|  | Compound 2 | Compound 3 | Compound 4 | Compound 5 | Compound 6 | Compound 7 |
|---|---|---|---|---|---|---|
| Cure Onset (° C.) | 161.6 | 65.9 | 100.4 | 103.5 | 158.2 | 110.4 |
| Cure Max (° C.) | 181.8 | 115.6 | 158.3 | 169.9 | 168.0 | 159.5 |
| Cure Energy (J/g) | 184.5 | 221.4 | 125.2 | 93.8 | 254.0 | 283.9 |
| $T_g$ (° C.) | 85.7 | 85.1 | 109.9 | 118.7 | 77.7 | 103.8 |

The results shown in Table 1 demonstrate that the relatively non-hindered Compound 3 had the earliest onset, and therefore the lowest latency in the group. The amine functional group in Compound 5 was more hindered than the amine function in Compound 4 and the cure onset and cure maximum were 10° C. and 21.5° C. higher for Compound 5, respectively.

Compounds 2 and 6 were more latent epoxy curatives in this test possessed. Both of these epoxy curatives had cure onsets around 160° C. The highest $T_g$ observed in the group of thermosets summarized in Table 1 was for the mixture based on Compound 5. Glass transition temperatures of thermoset compositions containing these curatives can be adjusted higher, if desired, through the use of polyfunctional epoxies and/or through the use of epoxy monomers with rigid backbones.

Example 9

Epoxy Compositions

Test compositions were prepared to compare the latency of some of the invention compounds to a control. The control used was 5-amino-1-naphthol (Sigma-Aldrich, Milwaukee, Wis.). This commercially available hybrid amine-phenol hardener was formulated with one equivalent of the bisphenol F diglycidyl ether as described in Example 8. The mixture was catalyzed with 0.4% Curezol C11Z-Azine (from Shikoku Chemicals Corporation, Japan). Similar test compositions were prepared where one equivalent of either Compound 2 or Compound 6 were used as the hardener (again with 0.4% C11Z-Azine catalyst). Initial viscosities were taken immediately after mixing and the compositions were then allowed to stage at 25° C. for 16 hours. The viscosities of all of the compositions were then measured again.

The mixture containing the 5-amino-1-naphthol hardener had increased in viscosity to 3.19 times (i.e. a 219% increase) its original value. The mixture containing Compound 2 had increased in viscosity by just 12% versus the initial value, and the composition based on Compound 6 had gone up in viscosity by only 6% after sixteen hours at room temperature. These results demonstrate an improvement in latency for the invention compounds versus a control hybrid amine-phenol epoxy hardener.

While this invention has been described with respect to these specific examples, it should be clear that other modifications and variations would be possible without departing from the spirit of this invention.

What is claimed is:

1. A compound selected from the group consisting of compounds having the structure of formula III:

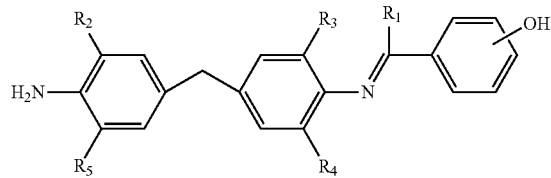

III wherein:

in compound III, $R_1$ is independently selected from the group consisting of methyl, ethyl, n-propyl, iso-propyl, a butyl, and phenyl, and each of $R_2$, $R_3$, $R_4$, and $R_5$ is independently selected from the group consisting of H, methyl, ethyl, n-propyl, iso-propyl, a butyl, and phenyl, wherein no more than two of $R_2$, $R_3$, $R_4$, and $R_5$ is H.

2. The compound of claim 1 selected from the group consisting of:

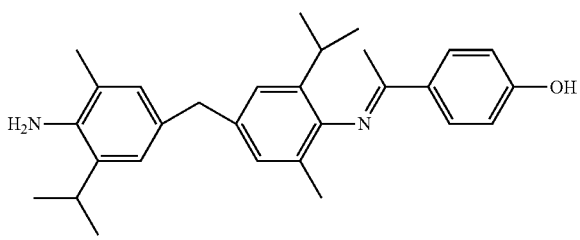

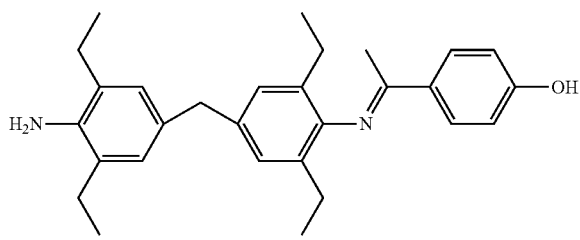

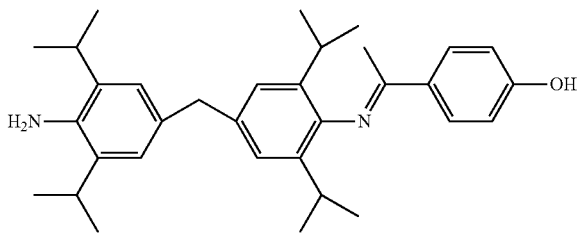

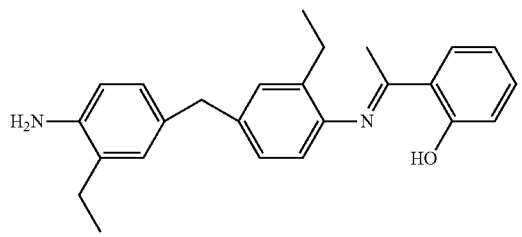

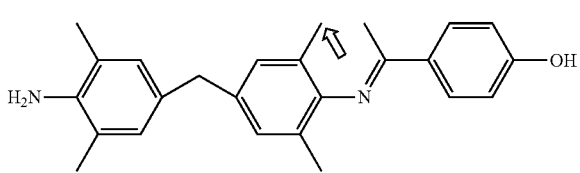

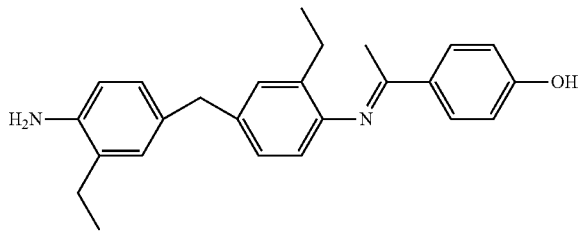

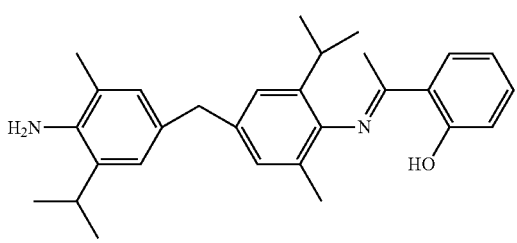

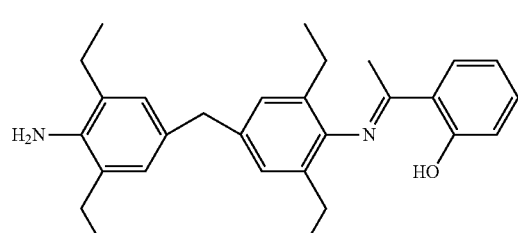

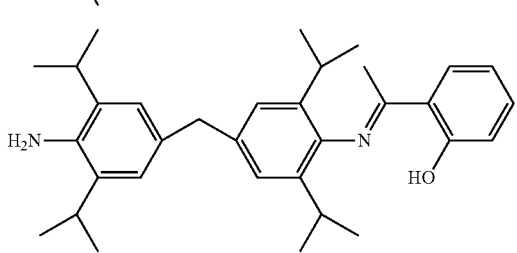

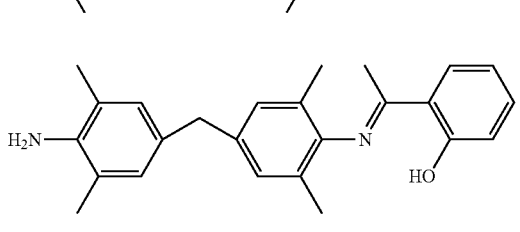

67 68
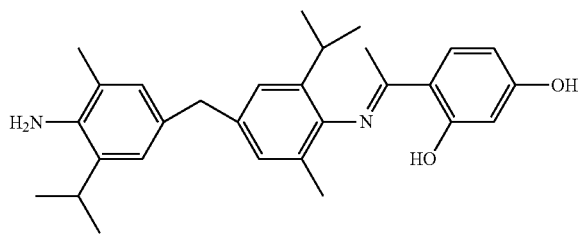 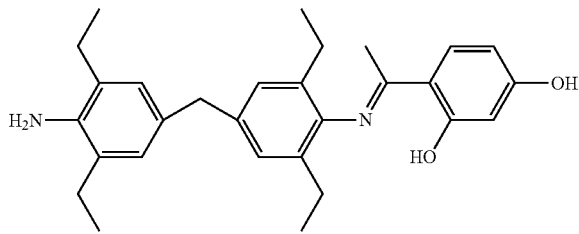
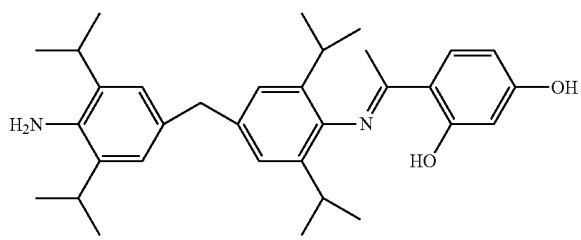 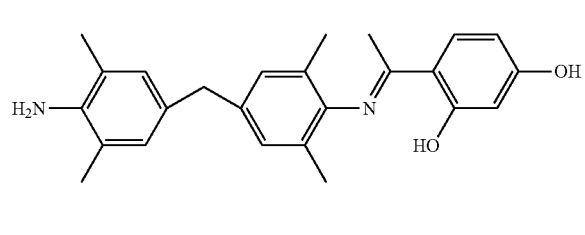
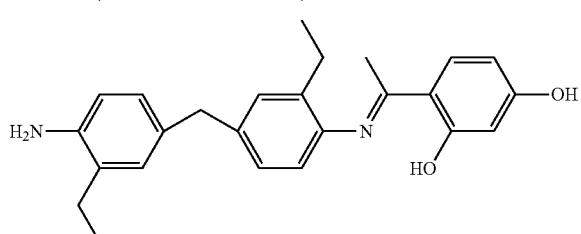 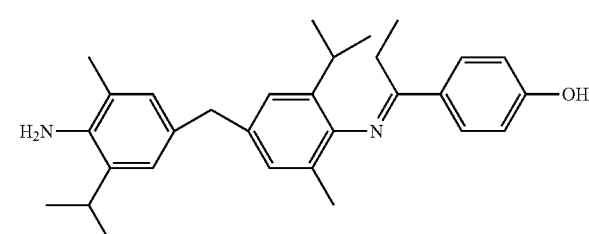
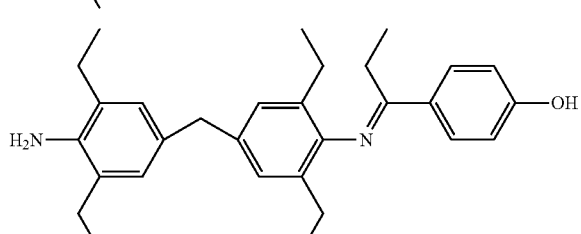 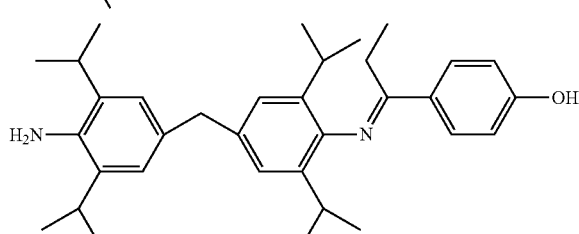
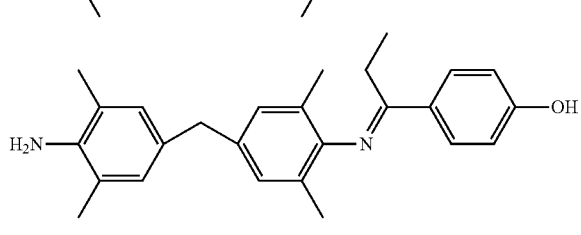 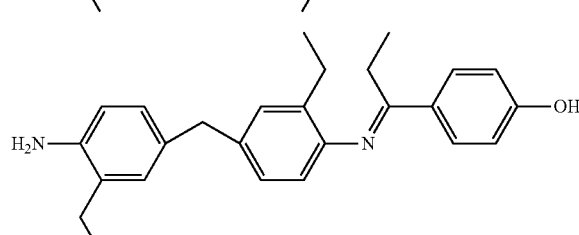
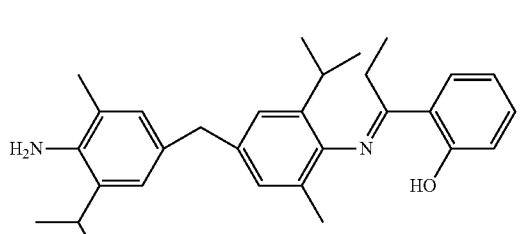 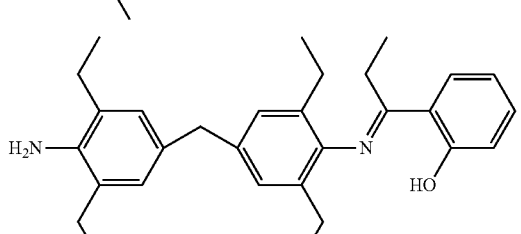
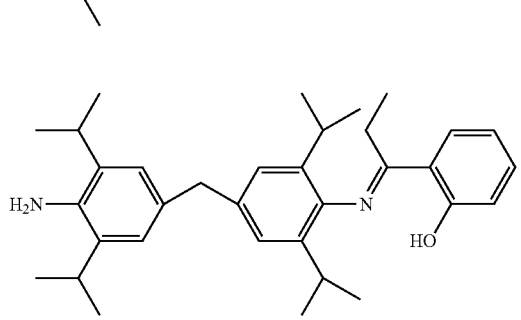 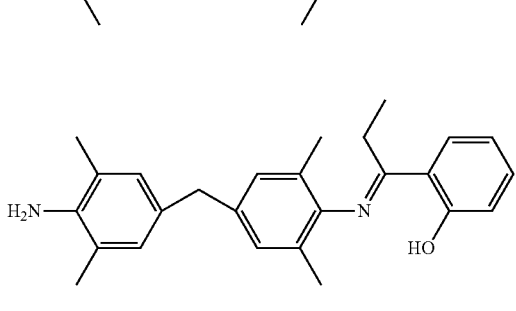

-continued
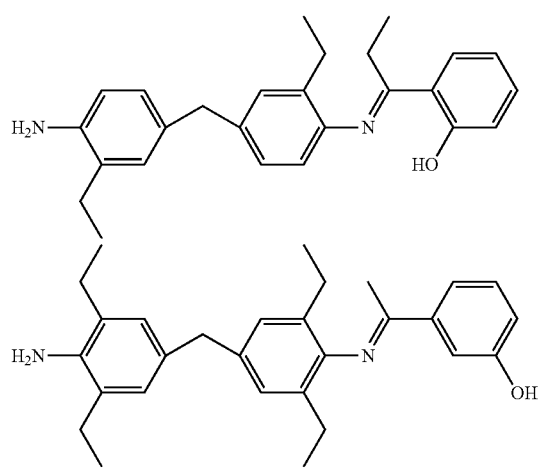
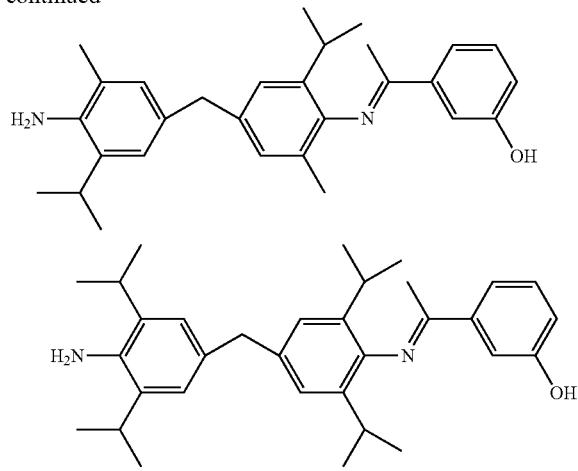
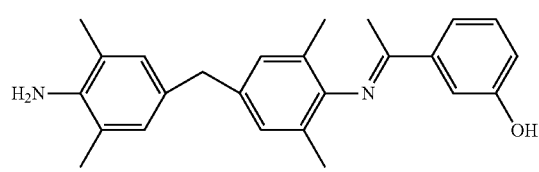
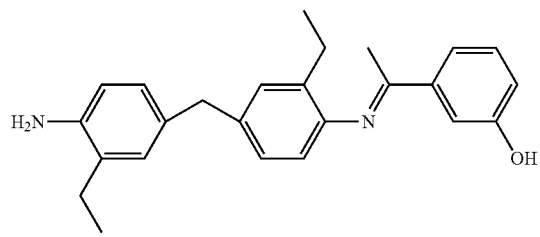
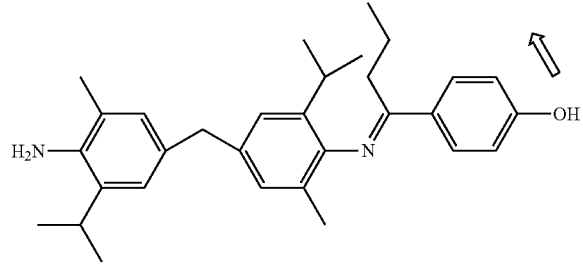
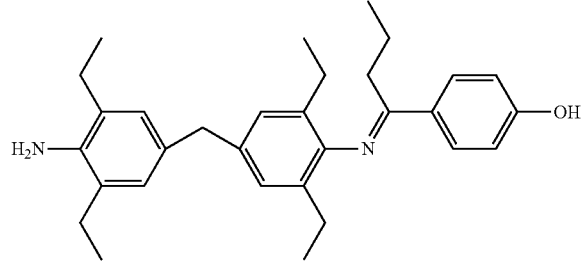
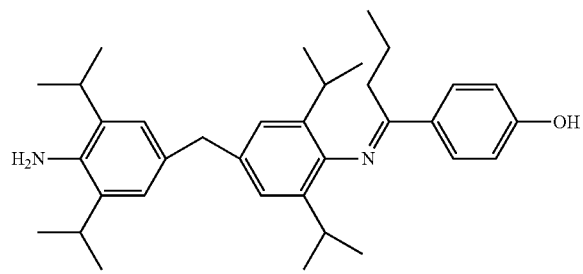
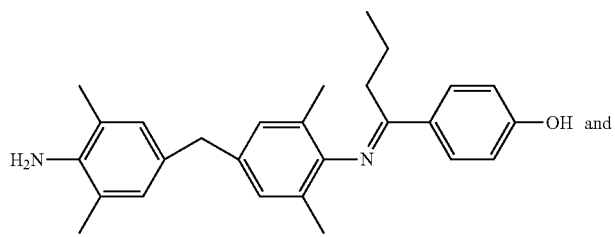
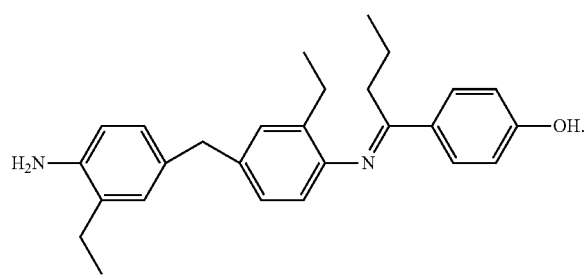

3. The compound of claim 1 selected from the group consisting of:

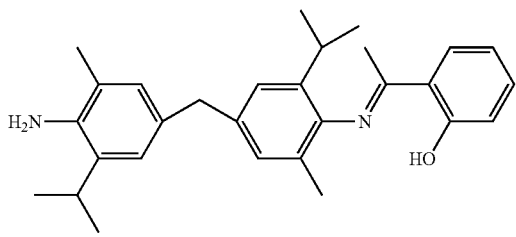

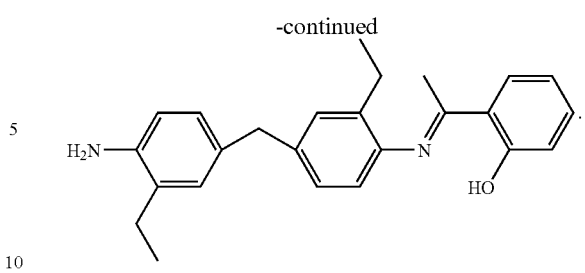

-continued

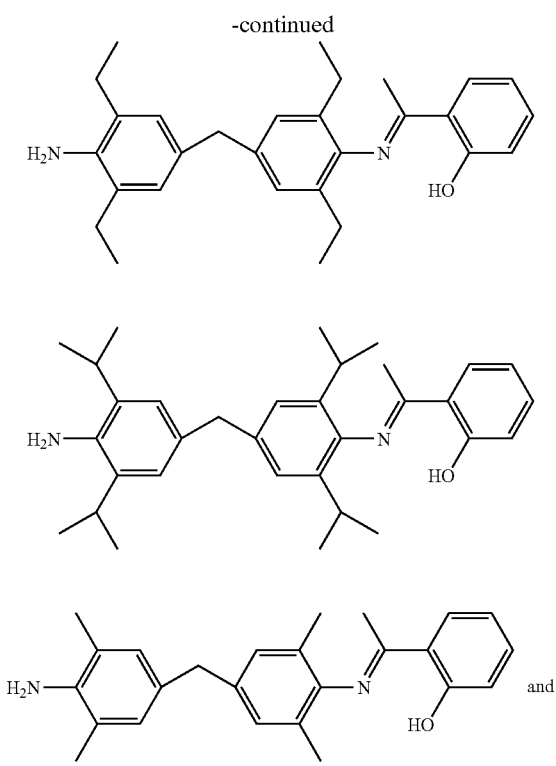

and

4. A method for preparing a composition comprising compounds having the structures of formulas III and IV, the method comprising reacting an aromatic diamine I with a carbonyl carrying compound II, according to the reaction scheme A:

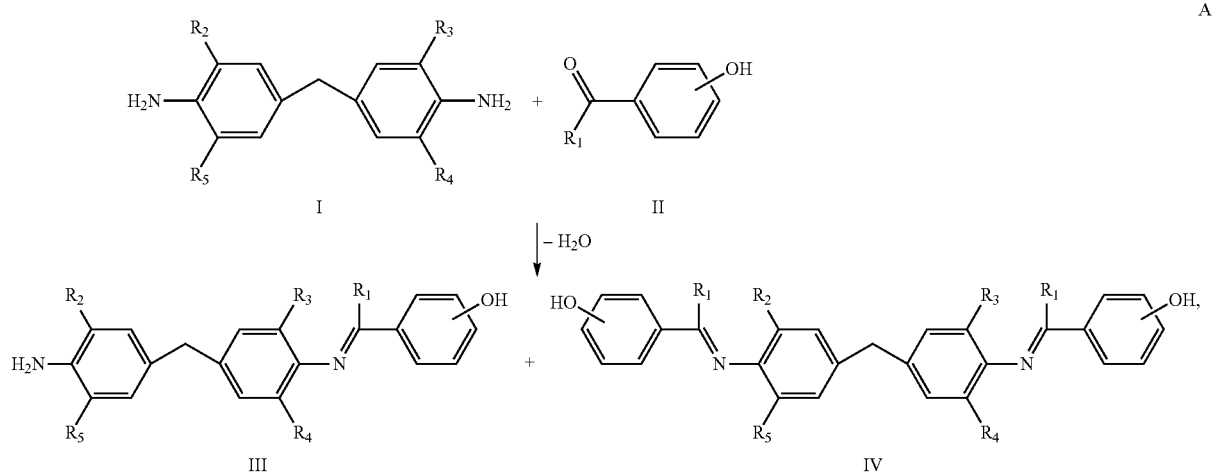

to thereby obtain the composition comprising compounds having the structures of formulas III and IV, wherein $R_1$, $R_2$, $R_3$, $R_4$ and $R_5$ are as defined in claim 1.

5. A method for preparing compounds having the structure of formula V, the method comprising hydrogenating a compound having the structure of formula III, according to the reaction scheme B:

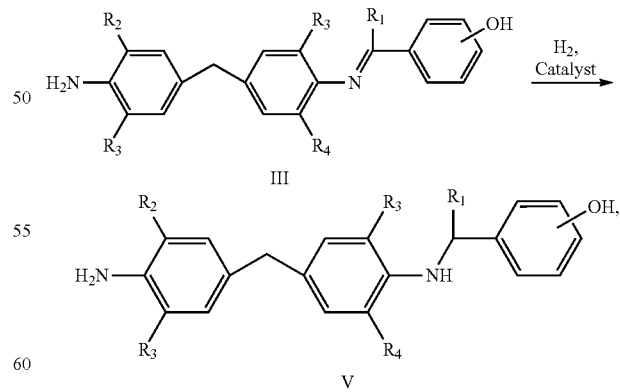

to thereby obtain compounds having the structure of formula V, wherein $R_1$, $R_2$, $R_3$, $R_4$, and $R_5$ are as defined in claim 1.

6. A composition comprising at least one epoxy resin and at least one compound of claim 1.

7. The composition of claim 6, wherein the composition is an adhesive.

8. The composition of claim 6, wherein the composition is an underfill composition.

9. The composition of claim 6, wherein the composition is B-stageable.

10. The composition of claim 6, wherein the composition is cured.

11. A method for curing an epoxy composition, comprising combining an epoxy resin with at least one compound of claim 1 under conditions favorable for curing the epoxy resin.

* * * * *